US009890365B2

(12) United States Patent
Wang et al.

(10) Patent No.: US 9,890,365 B2
(45) Date of Patent: *Feb. 13, 2018

(54) COMPOSITIONS USEFUL IN TREATMENT OF ORNITHINE TRANSCARBAMYLASE (OTC) DEFICIENCY

(71) Applicant: The Trustees of the University of Pennsylvania, Philadelphia, PA (US)

(72) Inventors: Lili Wang, Phoenixville, PA (US); James M. Wilson, Glen Mills, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/124,620

(22) PCT Filed: Mar. 9, 2015

(86) PCT No.: PCT/US2015/019536
§ 371 (c)(1),
(2) Date: Sep. 8, 2016

(87) PCT Pub. No.: WO2015/138357
PCT Pub. Date: Sep. 17, 2015

(65) Prior Publication Data
US 2017/0021037 A1 Jan. 26, 2017

Related U.S. Application Data

(60) Provisional application No. 61/950,157, filed on Mar. 9, 2014.

(51) Int. Cl.
*A61K 48/00* (2006.01)
*C12N 9/10* (2006.01)
*C12N 15/86* (2006.01)

(52) U.S. Cl.
CPC ........ *C12N 9/1018* (2013.01); *A61K 48/0058* (2013.01); *C12N 15/86* (2013.01); *C12Y 201/03003* (2013.01); *C12N 2710/10343* (2013.01); *C12N 2740/15043* (2013.01); *C12N 2750/14032* (2013.01); *C12N 2750/14033* (2013.01); *C12N 2750/14043* (2013.01); *C12N 2750/14071* (2013.01); *C12N 2750/14143* (2013.01); *C12N 2800/22* (2013.01)

(58) Field of Classification Search
None
See application file for complete search history.

(56) References Cited

U.S. PATENT DOCUMENTS

| | | |
|---|---|---|
| 5,139,941 A | 8/1992 | Muzyczka |
| 5,741,683 A | 4/1998 | Zhou |
| 5,866,552 A | 2/1999 | Wilson |
| 5,871,982 A | 2/1999 | Wilson |
| 6,057,152 A | 5/2000 | Samulski |
| 6,156,303 A | 12/2000 | Russell |
| 6,204,059 B1 | 3/2001 | Samulski |
| 6,251,677 B1 | 6/2001 | Wilson |
| 6,258,595 B1 | 7/2001 | Gao |
| 6,268,213 B1 | 7/2001 | Samulski |
| 6,274,354 B1 | 8/2001 | Wilson |
| 6,312,957 B1 | 11/2001 | Einerhand |
| 6,365,394 B1 | 4/2002 | Gao |
| 6,387,368 B1 | 5/2002 | Wilson |
| 6,399,385 B1 | 6/2002 | Croyle |
| 6,428,988 B1 | 8/2002 | Wilson |
| 6,468,524 B1 | 10/2002 | Chiorini |
| 6,475,769 B1 | 11/2002 | Wilson |
| 6,482,634 B1 | 11/2002 | Wilson |
| 6,485,966 B2 | 11/2002 | Gao |
| 6,491,907 B1 | 12/2002 | Rabinowitz |
| 6,596,535 B1 | 7/2003 | Carter |
| 6,660,514 B1 | 12/2003 | Zolotukhin |
| 6,759,237 B1 | 7/2004 | Wilson |
| 6,821,512 B1 | 11/2004 | Gao |
| 6,943,019 B2 | 9/2005 | Wilson |
| 6,951,753 B2 | 10/2005 | Shenk |
| 6,953,690 B1 | 10/2005 | Gao |
| 7,022,519 B2 | 4/2006 | Gao |
| 7,056,502 B2 | 6/2006 | Hildinger |
| 7,094,604 B2 | 8/2006 | Snyder |
| 7,115,391 B1 | 10/2006 | Chen |
| 7,125,717 B2 | 10/2006 | Carter |
| 7,172,893 B2 | 2/2007 | Rabinowitz |
| 7,198,951 B2 | 4/2007 | Gao |
| 7,201,898 B2 | 4/2007 | Monahan |
| 7,229,823 B2 | 6/2007 | Samulski |

(Continued)

FOREIGN PATENT DOCUMENTS

| | | |
|---|---|---|
| EP | 1310571 A2 | 5/2003 |
| EP | 2620161 | 7/2013 |

(Continued)

OTHER PUBLICATIONS

U.S. Appl. No. 61/570,708, filed Dec. 14, 2011, Bancel.
U.S. Appl. No. 61/950,157, filed Mar. 9, 2014, Wang.
Bantel-Schaal, Human Adeno-Associated Virus Type 5 Is only Distantly Related to Other known primate helper-dependent parvoviruses, Journal of Virology, vol. 73, No. 2, pp. 939-947, (Feb. 1999).
Calcedo et al, Serologic Characterization of Human and Non-Human Primate AAVs, Molecular Therapy, vol. 7, No. 5, Abstract 102. pp. S41, (May 2003).
Cazenave et al, RNA template-directed RNA synthesis by T7 RNA polymerase. Proceedings of the National Academy of Sciences 91.15 (Jul. 1994): 6972-6976.

(Continued)

*Primary Examiner* — Antonio Galisteo Gonzalez
(74) *Attorney, Agent, or Firm* — Howson & Howson LLP

(57) ABSTRACT

Non-viral delivery systems comprising engineered hOTC DNA and RNA sequences are provided which when delivered to a subject in need thereof are useful for treating hyperammonemia, ornithine transcarbamylase deficiency and symptoms associated therewith. Also provided are methods of using hOTC for treatment of liver fibrosis and/or cirrhosis in OTCD patients by administering hOTC.

15 Claims, 9 Drawing Sheets

(56) References Cited

U.S. PATENT DOCUMENTS

| | | |
|---|---|---|
| 7,238,526 B2 | 7/2007 | Wilson |
| 7,282,199 B2 | 10/2007 | Gao |
| 7,439,065 B2 | 10/2008 | Ferrari |
| 7,456,683 B2 | 11/2008 | Takano |
| 7,588,772 B2 | 9/2009 | Kay |
| 7,790,449 B2 | 9/2010 | Gao |
| 7,906,111 B2 | 3/2011 | Wilson |
| 7,985,565 B2 | 7/2011 | Mayer |
| 8,008,005 B2 | 8/2011 | Belshaw |
| 8,318,480 B2 | 11/2012 | Gao |
| 8,524,446 B2 | 9/2013 | Gao |
| 8,906,675 B2 | 12/2014 | Gao |
| 8,962,330 B2 | 2/2015 | Gao |
| 8,962,332 B2 | 2/2015 | Gao |
| 8,999,678 B2 | 4/2015 | Vandenberghe |
| 9,493,788 B2 | 11/2016 | Gao |
| 2002/0037867 A1 | 3/2002 | Wilson et al. |
| 2002/0090717 A1 | 7/2002 | Gao |
| 2003/0138772 A1 | 7/2003 | Gao |
| 2004/0086485 A1 | 5/2004 | Aguilar-Cordova |
| 2005/0112103 A1 | 5/2005 | Wilson |
| 2007/0015145 A1 | 1/2007 | Woolf |
| 2007/0036760 A1 | 2/2007 | Wilson |
| 2010/0323001 A1 | 12/2010 | Pachuk |
| 2011/0064763 A1 | 3/2011 | Allen |
| 2011/0184049 A1 | 7/2011 | Chuah |
| 2011/0236353 A1 | 9/2011 | Wilson |
| 2011/0281354 A1 | 11/2011 | Stayton |
| 2011/0286957 A1 | 11/2011 | Prieve |
| 2012/0195917 A1 | 8/2012 | Sahin |
| 2013/0045186 A1 | 2/2013 | Gao |
| 2013/0259924 A1 | 10/2013 | Bancel |
| 2015/0139953 A1 | 5/2015 | Gao |
| 2015/0159173 A1 | 6/2015 | Vandenberghe |
| 2015/0176027 A1 | 6/2015 | Gao |
| 2015/0315612 A1 | 11/2015 | Wilson |
| 2016/0097040 A1 | 4/2016 | Gao |
| 2016/0201088 A1 | 7/2016 | Gao |

FOREIGN PATENT DOCUMENTS

| | | |
|---|---|---|
| WO | WO 1996/000587 A1 | 1/1996 |
| WO | WO 1996/013598 A3 | 5/1996 |
| WO | WO 1998/009657 A2 | 3/1998 |
| WO | WO 1998/010086 A1 | 3/1998 |
| WO | WO 1998/010088 A1 | 3/1998 |
| WO | WO 1998/011244 | 3/1998 |
| WO | WO 1999/014354 A1 | 3/1999 |
| WO | WO 1999/015677 A1 | 4/1999 |
| WO | WO 1999/015685 A1 | 4/1999 |
| WO | WO 1999/047691 A1 | 9/1999 |
| WO | WO 1999/061601 A2 | 12/1999 |
| WO | WO 2000/028061 A3 | 5/2000 |
| WO | WO 2000/075353 A1 | 12/2000 |
| WO | WO 2001/023001 A2 | 4/2001 |
| WO | WO 2001/023597 A3 | 4/2001 |
| WO | WO 2001/025462 A1 | 4/2001 |
| WO | WO 2001/040455 A3 | 6/2001 |
| WO | WO 2001/070276 A2 | 9/2001 |
| WO | WO 2001/083692 A2 | 11/2001 |
| WO | WO 2002/018659 A2 | 3/2002 |
| WO | WO 2003/042397 | 5/2003 |
| WO | WO 2003/104392 A2 | 12/2003 |
| WO | WO 2005/033321 | 4/2005 |
| WO | WO 2006/110689 | 10/2006 |
| WO | WO 2010/053572 | 5/2010 |
| WO | WO 2011/126808 | 10/2011 |
| WO | WO 2012/170930 | 12/2012 |
| WO | WO 2013/049493 | 4/2013 |
| WO | WO 2013/063468 | 5/2013 |
| WO | WO 2013/143555 A1 | 10/2013 |
| WO | WO 2013/151666 | 10/2013 |
| WO | WO 2013/182683 | 12/2013 |
| WO | WO 2015/017519 | 2/2015 |
| WO | WO 2015/138348 A1 | 9/2015 |
| WO | WO 2015/138357 | 9/2015 |

OTHER PUBLICATIONS

Chiorini et al, Cloning and Characterization of Adeno-Associated Virus Type 5, Journal of Virology, vol. 73, No. 2, pp. 1309-1319, (Feb. 1999).

Chirmule et al, Humoral Immunity to Adeno-Associated Virus Type 2 Vectors following Administration to Murine and Nonhuman Primate Muscle, Journal of Virology, vol. 74, No. 5, pp. 2420-2425, (Mar. 2000).

Cronin et al, Efficient transduction and optogenetic stimulation of retinal bipolar cells by a synthetic adeno-associated virus capsid and promoter, EMBO Molecular Medicine, published online Aug. 4, 2014, 6(9):1175-1190.

Cunningham et al, AAV2/8-mediated correction of OTC deficiency is robust in adult but not neonatal Spf$^{ash}$ mice. Molecular Therapy, published Apr. 21, 2009. 17.8 (2009): 1340-1346.

De et al, Therapeutic Levels for 1-Antitrypsin Following Intrapleural Administration of a Non-human Primate Serotype rh10 AAV Vector Expressing 1-Antitrypsin, 7th Annual Meeting of the American Society of Gene Therapy [Jun. 2-6, 2004], Minneapolis, Minnesota, Abstract 338, (e-publ. May 2, 2004).

Fagone et al, Systemic errors in quantitative PCR titration of self-complementary AAV vectors and improved alternative methods. Human gene therapy methods 23.1 (2012): 1. Published online Aug. 16, 2011.

Forslund et al, A Broad Range of Human Papillomavirus Types Detected with a General PCR Method Suitable for Analysis of Cutaneous Tumours and Normal Skin, Journal of General Virology, vol. 80, No. 9, pp. 2437-2443, (Sep. 9, 1999).

Gao et al, Clades of Adeno-Associated Viruses are Widely Disseminated in Human Tissues, Journal of Virology, vol. 78, No. 12, pp. 6381-6388 (Jun. 2004).

Gao et al, Diversity of Latent AAV Genomes in Non-Human Primate and Human Tissues, Molecular Therapy, vol. 7, No. 5, Abstract 400. pp. S 158, (May 2003).

Gao et al, Erythropoietin Gene Therapy Leads to Autoimmune Anemia in Macaques, Blood, vol. 103, No. 9, (May 1, 2004).

Gao et al, Novel Adeno-Associated Viruses from Rhesus Monkeys as Vectors for Human Gene Therapy, PNAS, vol. 99, No. 18, pp. 11854-11859, (Sep. 3, 2002).

Gordeeva et al, Improved PCR-based gene synthesis method and its application to the Citrobacter freundii phytase gene codon modification. Journal of microbiological methods 81.2 (2010): 147-152. Epub Mar 10, 2010.

Hamar et al, Small interfering RNA targeting Fas protects mice against renal ischemia-reperfusion injury. Proceedings of the National Academy of Sciences of the United States of America 101.41 (2004): 14883-14888, Epub Oct. 4, 2004.

Kassim et al, Adeno-associated virus serotype 8 gene therapy leads to significant lowering of plasma cholesterol levels in humanized mouse models of homozygous and heterozygous familial hypercholesterolemia, Human Gene Therapy Epub Nov. 14, 2012, 24(1): 19-26.

Kassim et al, Gene Therapy in a Humanized Mouse Model of Familial Hypercholesterolemia Leads to Marked Regression of Atherosclerosis, PLoS One, Oct. 19, 2010, vol. 5, Issue 10, pp. e13424 (10 pp.) and Supplementary Data (1 page).

Khoury et al, Efficient new cationic liposome formulation for systemic delivery of small interfering RNA silencing tumor necrosis factor α in experimental arthritis. Arthritis & Rheumatism 54.6 (2006): 1867-1877. (First published: May 25, 2006).

Kim et al, Acute treatment of hyperammonemia by continuous renal replacement therapy in a newborn patient with ornithine transcarbamylase deficiency. Korean journal of pediatrics 54.1.0 (2011): 425-428. (Published online Oct. 31, 2011).

Krieg et al, Functional messenger RNAs are produced by SP6 in vitro transcription of cloned cDNAs, Nucleic Acids Research Sep. 25, 1984;12(18):7057-70.

(56) References Cited

OTHER PUBLICATIONS

Kudla et al, High guanine and cytosine content increases mRNA levels in mammalian cells. PLoS Biol 4.6 (2006): e180. (Published: May 23, 2006).

Landen et al, Intraperitoneal delivery of liposomal siRNA for therapy of advanced ovarian cancer. Cancer biology & therapy 5.12 (2006): 1708-1713. Published online: Dec. 31, 2006.

Lebherz et al, Gene Therapy with Novel Adeno-Associated Virus Vectors Substantially Diminishes Atherosclerosis in a Murine Model of Familial Hypercholesterolemia, The Journal of Gene Medicine, vol. 6, No. 6, pp. 663-672, (Jun. 2004).

Limberis et al, A Novel AAV Vector for the Treatment of Cystic Fibrosis Airway Disease, 7th Annual Meeting of the American Society of Gene Therapy [Jun. 2-6, 2004] Minneapolis, Minnesota, Abstract 692, (e-publ. May 2, 2007).

Lock et al, Rapid, simple, and versatile manufacturing of recombinant adeno-associated viral vectors at scale. Human gene therapy 21.10 (2010): 1259-1271. (Published online Sep. 24, 2010).

Lu et al, Analysis of Homologous Recombination Between different AAV Genomes in In Vitro Co-Infections, Molecular Therapy, vol. 7, No. 5, Abstract 38. pp. S15, (May 2003).

McCarty et al, Self-complementary recombinant adeno-associated virus (scAAV) vectors promote efficient transduction independently of DNA synthesis. Gene therapy 8.16 (2001):1248-1254. (Aug. 2001).

Mian et al, Long-term correction of ornithine transcarbamylase deficiency by WPRE-mediated overexpression using a helper-dependent adenovirus. Molecular Therapy 10.3 (2004): 492-499. (Sep. 2004).

Miyatake et al, Transcriptional targeting of herpes simplex virus for cell-specific replication. Journal of virology 71.7 (1997): 5124-5132. (Jul. 1997).

Mizukami et al, AAV 8 Mediated Transgene Expression in Mice and Non-Human Primates, American Society of Gene Therapy, 9th Annual Meeting, Abstract, (May 31-Jun. 4, 2006).

Morizono et al, Mammalian N-acetylglutamate synthase. Molecular genetics and metabolism 81 (2004): 4-11. (Apr. 2004).

Morrissey et al, Activity of stabilized short interfering RNA in a mouse model of hepatitis B virus replication. Hepatology 41.6 (2005): 1349-1356. First published on May 2, 2005.

Moscioni et al, Long-term correction of ammonia metabolism and prolonged survival in ornithine transcarbamylase-deficient mice following liver-directed treatment with adeno-associated viral vectors. Molecular Therapy 14.1 (2006): 25-33. Published Jul. 1, 2006.

Numata et al, Paternal transmission and slow elimination of mutant alleles associated with late-onset ornithine transcarbamylase deficiency in male patients. Journal of human genetics 53.1 (2008): 10-17. (Nov. 20, 2007).

Rick et al, Congenital Bleeding Disorders, American Society of Hematology, vol. (1), pp. 559-574 (Jan. 1, 2003).

Rutledge et al, Infectious Clones and Vectors Derived from Adeno-Associated Virus (AAV) Serotypes Other than AAV Type 2, Journal of Virology, vol. 72, No. 1. pp. 309-319 (Jan. 1998).

Sandig et al, HBV-derived promoters direct liver-specific expression of an adenovirally transduced LDL receptor Gene, Gene Ther., 3:1002-9 (1996). (Nov. 1996).

Sanmiguel et al, Real-Time PCR as an Analytic Tool in Gene Therapy, Molecular Therapy, vol. 7, No. 5, Abstract 913. pp. S352, (May 2003).

Sarkar et al, Total Correction of Hemophilia A Mice with Canine FVIII Using an AAV 8 Serotype, Blood First Edition Paper, 103(4), pp. 1253-1260, (Oct. 9, 2003).

Soutschek et al, Therapeutic silencing of an endogenous gene by systemic administration of modified siRNAs. Nature 432.7014 (2004): 173-178. Published Nov. 11, 2004.

Spada et al, 161-P: Novel OTC gene deletion and somatic mosaicism in a boy with late onset OTC deficiency and early liver cirrhosis. Journal of inherited metabolic disease, vol. 26, Suppl. 2, 81 (2003). Published Sep. 1, 2003.

Su et al, In vitro and in vivo mRNA delivery using lipid-enveloped pH-responsive polymer nanoparticles. Molecular pharmaceutics 8.3 (2011): 774-787; web publication: Mar. 21, 2011.

Sun et al, Efficacy of an Adeno-Associated Virus 8-Pseudotyped Vector in Glycogen Storage Disease Type II, Molecular Therapy, vol. 11, No. 1, pp. 57-65, (Jan. 2005).

Thompson et al, A comprehensive comparison of multiple sequence alignment programs. Nucleic acids research 27.13 (1999): 2682-2690. (Jul. 1999).

Tuchman et al, Cross-sectional multicenter study of patients with urea cycle disorders in the United States. Molecular genetics and metabolism 94.4 (2008): 397-402. Epub Jun. 17, 2008.

Uchida et al, In vivo messenger RNA introduction into the central nervous system using polyplex nanomicelle. PLoS One 8.2 (Feb. 2013): e56220.

Vandenberghe et al, AAV Clades: Their Ability to Recombine and Cross Species-Barriers, 7th Annual Meeting of The American Society of Gene Therapy [Jun. 2-6, 2004] Minneapolis, Minnesota, Abstract 88, (e-publ. May 2, 2004).

Vandenberghe et al, Structure-Function Relationship of the Novel Non-Human Primate Adeno-Associated Viruses, Molecular Therapy, vol. 7, No. 5, Abstract 99, pp. S40, (May 2003).

Wang et al, Neonatal Gene Therapy for OTC Deficiency. Molecular Therapy. vol. 20. 75 Varick St, 9th Flr, New York, NY 10013-1917 USA: Nature Publishing Group, published May 1, 2012. ISSN: 1525-0016, DOI: 10.1038/mt.2012.86.

Wang et al, Preclinical evaluation of a clinical candidate AAV8 vector for ornithine transcarbamylase (OTC) deficiency reveals functional enzyme from each persisting vector genome, Molec. Gen. and Metabolism, published online Oct. 31, 2011, 2012(105):203-211.

Wang et al, Production of AAV Vectors with Different Serotypes, Molecular Therapy, vol. 7, No. 5, Abstract 906. pp. S350, (May 2003).

Wang et al, Sustained correction of OTC deficiency in spfash mice using optimized self-complementary AAV-2/8 vectors, Gene Therapy, published online Aug. 18, 2011, 2012(19):404-410.

Wang et al, Systematic evaluation of AAV vectors for liver directed gene transfer in murine models. Molecular Therapy, published Oct. 27, 2009, 18.1 (2010): 118-125.

Wichlacz et al, Generating in vitro transcripts with homogenous 3' ends using trans-acting antigenomic delta ribozyme. Nucleic acids research, Published online Feb. 18, 2004;32(3):e39.

Wilson et al, Hepatocellular carcinoma in a research subject with ornithine transcarbamylase deficiency. Molecular genetics and metabolism 105.2 (2012): 263-265. Published Oct. 25, 2011.

Xiao et al, Gene Therapy Vectors Based on Adeno-Associated Virus Type 1, Journal of Virology, vol. 73, No. 5, pp. 3994-4003, (May 1999).

Xiao et al, Production of High-Titer Recombinant Adeno-Associated Virus Vectors in the Absence of Helper Adenovirus, vol. 72, No. 3, pp. 2224-2232, (Mar. 1998).

Xiong et al. PCR-based accurate synthesis of long DNA sequences. Nature protocols 1.2 (2006): 791-797. Published online: Jul. 13, 2006.

Yamaguchi et al, Mutations and polymorphisms in the human ornithine transcarbamylase (OTC) gene. Human mutation 27.7 (2006): 626-632, Published Jul. 1, 2006.

Yaplito-Lee et al, Histopathological findings in livers of patients with urea cycle disorders. Molecular genetics and metabolism 108.3 (2013): 161-165. Epub Jan. 23, 2013.

Ye et al, Differences in the human and mouse amino-terminal leader peptides of ornithine transcarbamylase affect mitochondrial import and efficacy of adenoviral vectors. Human gene therapy 12.9 (2001): 1035-1046. Published Jan. 23, 2013.

Ye et al, Prolonged metabolic correction in adult ornithine transcarbamylase-deficient mice with adenoviral vectors. Journal of Biological Chemistry 271.7 (1996): 3639-3646. (Feb. 1996).

Young et al, Two-step total gene synthesis method. Nucleic acids research 32.7 (2004): e59-e59. Published online Apr. 15, 2004.

Yu et al, Recent patents on oligonucleotide synthesis and gene synthesis. Recent patents on DNA & gene sequences 6.1 (2012): 10-21.(Apr. 2012).

(56) References Cited

OTHER PUBLICATIONS

Zanta-Boussif et al, Validation of a mutated PRE sequence allowing high and sustained transgene expression while abrogating WHV-X protein synthesis: application to the gene therapy of WAS. Gene therapy 16.5 (2009): 605-619. Published online Mar. 5, 2009.
Zhang et al, Adenovirus-adeno-associated virus hybrid for large-scale recombinant adeno-associated virus production, Human Gene Therapy 20.9 (2009): 922-929. Published online Jul. 20, 2009.
Zhong at al, Recombinant adeno-associated virus integration sites in murine liver after ornithine transcarbamylase gene correction. Human gene therapy 24.5 (2013): 520-525. Published May 1, 2013.
Zhou et al, Direct Rescue and Cloning of Infectious Novel AAV Genomes from Non-Human Primate Tissues, Molecular Therapy, vol. 7, No. 5, Abstract 907. pp. S350, (May 2003).
Zhou et al, Evaluation of Novel Gene Transfer Vectors Derived from Infectious Molecular Clones of Primate AAVs, 7" Annual Meeting of The American Society of Gene Therapy [Jun. 2-6, 2004] Minneapolis, Minnesota, Abstract 90, (e-publ. May 2, 2004).
UniProtKB_P00480, Ornithine carbamoyltransferase, mitochondrial, Last Sequence Update: Dec. 20, 2005 [online]. [Retrieved on Aug. 5, 2015 from the Internet: http://www.uniprot.org/uniprot/P00480].
Zhang et al. Zhang and Henzel Original 270 Entries Dataset, retrieved from http://proline.bic.nus.edu.sg/spdb/zhang270.htm on Nov. 29, 2016.
Lichter-Konecki et al. Ornithine Transcarbamylase Deficiency. Aug. 29, 2013 [Updated Apr. 14, 2016]. GeneReviews® [Internet]. Seattle (WA): University of Washington, Seattle; 1993-2016. retrieved from: https://www.ncbi.nlm.nih.gov/books/NBK154378/ on Nov. 29, 2016.
Requirement for Restriction/Election dated Jun. 11, 2015 issued in U.S. Appl. No. 14/598,462.
Applicant's Response filed Aug. 11, 2015 to the Requirement for Restriction/Election dated Jun. 11, 2015 issued in U.S. Appl. No. 14/598,462.
Office Action dated Nov. 20, 2015 issued in U.S. Appl. No. 14/598,462.
Applicant's Response filed Apr. 20, 2016 to the Office Action dated Nov. 20, 2015 issued in U.S. Appl. No. 14/598,462.
Notice of Allowance and Fee(s) Due dated Jul. 15, 2016 issued in U.S. Appl. No. 14/598,462.
U.S. Appl. No. 15/122,853, filed Aug. 31, 2016.
International Search Report and Written Opinion of the International Searching Authority issued on PCT/US2015/019513, dated Jun. 10, 2015.
International Search Report and Written Opinion of the International Searching Authority issued on PCT/US2015/019536, dated Oct. 8, 2015.
U.S. Appl. No. 15/298,760, filed Oct. 20, 2016.
U.S. Appl. No. 15/227,418, filed Aug. 3, 2016.
Office Action dated Sep. 8, 2017 issued in U.S. Appl. No. 15/122,853.
Applicant's Response filed Jul. 31, 2017 to the Requirement for Restriction/Election dated May 30, 2017 issued in U.S. Appl. No. 15/122,853.
Requirement for Restriction/Election dated May 30, 2017 issued in U.S. Appl. No. 15/122,853.

FIG. 1A

```
   1 atgctgttta atctgaggat cctgttaaac aatgcagctt ttagaaatgg tcacaacttc
  61 atggttcgaa attttcggtg tggacaacca ctacaaaata aagtgcagct gaagggccgt
 121 gaccttctca ctctaaaaaa ctttaccgga gaagaaatta aatatatgct atggctatca
 181 gcagatctga aatttaggat aaaacagaaa ggagagtatt tgcctttatt gcaagggaag
 241 tccttaggca tgatttttga gaaaagaagt actcgaacaa gattgtctac agaaacaggc
 301 tttgcacttc tgggaggaca tccttgtttt cttaccacac aagatattca tttgggtgtg
 361 aatgaaagtc tcacggacac ggcccgtgta ttgtctagca tggcagatgc agtattggct
 421 cgagtgtata aacaatcaga tttggacacc ctggctaaag aagcatccat cccaattatc
 481 aatgggctgt cagatttgta ccatcctatc cagatcctgg ctgattacct cacgctccag
 541 gaacactata gctctctgaa aggtcttacc ctcagctgga tcggggatgg gaacaatatc
 601 ctgcactcca tcatgatgag cgcagcgaaa ttcggaatgc accttcaggc agctactcca
 661 aagggttatg agccggatgc tagtgtaacc aagttggcag agcagtatgc caaagagaat
 721 ggtaccaagc tgttgctgac aaatgatcca ttggaagcag cgcatggagg caatgtatta
 781 attacagaca cttggataag catgggacaa gaagaggaga agaaaaagcg gctccaggct
 841 ttccaaggtt accaggttac aatgaagact gctaaagttg ctgcctctga ctggacattt
 901 ttacactgct gcccagaaa gccagaagaa gtggatgatg aagtctttta ttctcctcga
 961 tcactagtgt tcccagaggc agaaaacaga aagtggacaa tcatggctgt catggtgtcc
1021 ctgctgacag attactcacc tcagctccag aagcctaaat tt
```

FIG. 1B

```
Met Leu Phe Asn Leu Arg Ile Leu Leu Asn Asn Ala Ala Phe Arg Asn
1               5                   10                  15

Gly His Asn Phe Met Val Arg Asn Phe Arg Cys Gly Gln Pro Leu Gln
            20                  25                  30

Asn Lys Val Gln Leu Lys Gly Arg Asp Leu Leu Thr Leu Lys Asn Phe
        35              40                  45

Thr Gly Glu Glu Ile Lys Tyr Met Leu Trp Leu Ser Ala Asp Leu Lys
    50              55                  60

Phe Arg Ile Lys Gln Lys Gly Glu Tyr Leu Pro Leu Leu Gln Gly Lys
65              70                  75                      80

Ser Leu Gly Met Ile Phe Glu Lys Arg Ser Thr Arg Thr Arg Leu Ser
            85                  90                  95

Thr Glu Thr Gly Phe Ala Leu Leu Gly Gly His Pro Cys Phe Leu Thr
            100                 105                 110

Thr Gln Asp Ile His Leu Gly Val Asn Glu Ser Leu Thr Asp Thr Ala
        115                 120                 125

Arg Val Leu Ser Ser Met Ala Asp Ala Val Leu Ala Arg Val Tyr Lys
    130                 135                 140

Gln Ser Asp Leu Asp Thr Leu Ala Lys Glu Ala Ser Ile Pro Ile Ile
145                 150                 155                 160

Asn Gly Leu Ser Asp Leu Tyr His Pro Ile Gln Ile Leu Ala Asp Tyr
                165                 170                 175

Leu Thr Leu Gln Glu His Tyr Ser Ser Leu Lys Gly Leu Thr Leu Ser
            180                 185                 190
```

FIG. 1C

```
Trp Ile Gly Asp Gly Asn Asn Ile Leu His Ser Ile Met Met Ser Ala
        195                 200                 205

Ala Lys Phe Gly Met His Leu Gln Ala Ala Thr Pro Lys Gly Tyr Glu
    210                 215                 220

Pro Asp Ala Ser Val Thr Lys Leu Ala Glu Gln Tyr Ala Lys Glu Asn
225                 230                 235                 240

Gly Thr Lys Leu Leu Leu Thr Asn Asp Pro Leu Glu Ala Ala His Gly
                245                 250                 255

Gly Asn Val Leu Ile Thr Asp Thr Trp Ile Ser Met Gly Gln Glu Glu
                260                 265                 270

Glu Lys Lys Lys Arg Leu Gln Ala Phe Gln Gly Tyr Gln Val Thr Met
        275                 280                 285

Lys Thr Ala Lys Val Ala Ala Ser Asp Trp Thr Phe Leu His Cys Leu
    290                 295                 300

Pro Arg Lys Pro Glu Glu Val Asp Asp Glu Val Phe Tyr Ser Pro Arg
305                 310                 315                 320

Ser Leu Val Phe Pro Glu Ala Glu Asn Arg Lys Trp Thr Ile Met Ala
                325                 330                 335

Val Met Val Ser Leu Leu Thr Asp Tyr Ser Pro Gln Leu Gln Lys Pro
                340                 345                 350

Lys Phe
```

FIG. 2

```
   1 atgctgttca acctgcgaat cctgctgaac aatgccgctt ttcggaacgg gcacaatttc
  61 atggtgagga actttcgctg cggacagccc ctccagaaca aggtccagct gaagggcagg
 121 gacctgctga ccctgaaaaa tttcacaggg gaggaaatca agtacatgct gtggctgtca
 181 gccgatctga agttccggat caagcagaag ggcgaatatc tgcctctgct ccagggcaaa
 241 agcctgggga tgatcttcga aaagcgcagt actcggacca gactgtcaac agagactgga
 301 ttcgcactgc tgggaggaca cccatgtttt ctgaccacac aggacattca tctgggagtg
 361 aacgagtccc tgaccgacac agcacgcgtc ctgagctcca tggctgatgc agtgctggct
 421 cgagtctaca acagtctgac ctggatacc ctggccaagg aagcttctat cccaatcatt
 481 aatggcctga gtgacctgta tcacccatc cagattctgg ccgattacct gaccctccag
 541 gagcattatt ctagtctgaa agggctgaca ctgagctgga ttggggacgg aaacaatatc
 601 ctgcactcca ttatgatgag cgccgccaag tttggaatgc acctccaggc tgcaaccccca
 661 aaaggctacg aacccgatgc ctccgtgaca aagctggcag aacagtatgc aaagagaac
 721 ggcactaagc tgctgctgac caatgaccct ctggaggccg ctcacggagg caacgtgctg
 781 atcactgata cctggattag tatgggacag gaggaagaga agaagaagcg gctccaggcc
 841 ttccagggct accaggtgac aatgaaaact gctaaggtcg cagccagcga ctggaccttt
 901 ctgcattgcc tgcccagaaa gcctgaagag gtggacgatg aggtcttcta ctcacccaga
 961 agcctggtgt ttcctgaagc tgagaatagg aagtggacaa tcatggcagt gatggtcagc
1021 ctgctgactg attattcccc tcagctccag aaaccaaagt tctgataa
```

FIG. 3

```
   1  ctgcagccgc caccatgctg ttcaacctgc gaatcctgct gaacaacgcc gcttttcgga
  61  acgggcacaa ctttatggtg aggaactttc gctgcggaca gcccctccag aataaggtcc
 121  agctgaaggg cagggacctg ctgaccctga aaaatttcac aggggaggaa atcaagtata
 181  tgctgtggct gtcagctgat ctgaagttcc ggatcaagca gaagggcgaa tatctgcctc
 241  tgctccaggg caaaagcctg gggatgatct tcgaaaagcg cagtactcgg accagactgt
 301  caaccgagac tggattcgct ctgctgggag gacacccttg ttttctgacc actcaggaca
 361  ttcacctggg agtgaacgag tccctgaccg acactgctcg cgtcctgagc tctatggccg
 421  acgctgtgct agctcgagtc tacaaacagt ccgacctgga taccctggcc aaggaagctt
 481  ctatcccaat tattaacggc ctgtcagacc tgtatcaccc catccagatt ctggccgatt
 541  acctgaccct ccaggagcac tattctagtc tgaaagggct gacactgagt tggattgggg
 601  acggaaacaa tatcctgcac tctattatga tgtcagccgc caagtttgga atgcacctcc
 661  aggctgcaac cccaaaaggc tacgaacccg atgcctcagt gacaaagctg gctgaacagt
 721  acgccaaaga gaacggcact aagctgctgc tgaccaacga ccctctggag gccgctcacg
 781  gaggcaacgt gctgatcacc gatacctgga ttagtatggg acaggaggaa gagaagaaga
 841  agcggctcca ggccttccag ggctaccagg tgacaatgaa aaccgctaag gtcgcagcca
 901  gcgattggac ctttctgcac tgcctgccca gaaagcccga gaggtggac gacgaggtct
 961  tctactctcc cagaagcctg gtgtttcccg aagctgagaa taggaagtgg acaattatgg
1021  cagtgatggt cagcctgctg actgattatt cacctcagct ccagaaacca aagttctgat
1081  aagcggccgc
```

FIG. 4

```
   1 ctgcagccgc caccatgctg ttcaacctgc gaatcctgct gaacaacgcc gcttttcgga
  61 acgggcacaa ctttatggtg aggaactttc gctgcggaca gcccctccag aataaggtcc
 121 agctgaaggg cagggacctg ctgaccctga aaaatttcac aggggaggaa atcaagtata
 181 tgctgtggct gtcagctgat ctgaagttcc ggatcaagca gaagggcgaa tatctgcctc
 241 tgctccaggg caaaagcctg gggatgatct tcgaaaagcg cagtactcgg accagactgt
 301 caaccgagac tggattcgct ctgctgggag gacacccttg ttttctgacc actcaggaca
 361 ttcacctggg agtgaacgag tccctgaccg acactgctcg cgtcctgagc tctatggccg
 421 acgctgtgct ggctcgagtc tacaaacagt ccgacctgga taccctggcc aaggaagctt
 481 ctatcccaat tattaacggc ctgtcagacc tgtatcaccc catccagatt ctggccgatt
 541 acctgaccct ccaggagcac tattctagtc tgaaagggct gacactgagt tggattgggg
 601 acggaaacaa tatcctgcac tctattatga tgtcagccgc caagtttgga atgcacctcc
 661 aggctgcaac cccaaaaggc tacgaacccg atgcctcagt gacaaagctg gctgaacagt
 721 acgccaaaga gaacggcact aagctgctgc tgaccaacga ccctctggag gccgctcacg
 781 gaggcaacgt gctgatcacc gatacctgga ttagtatggg acaggaggaa gagaagaaga
 841 agcggctcca ggccttccag ggctaccagg tgacaatgaa aaccgctaag gtcgcagcca
 901 gcgattggac ctttctgcac tgcctgccca gaaagcccga agaggtggac gacgaggtct
 961 tctactctcc cagaagcctg gtgtttcccg aagctgagaa taggaagtgg acaattatgg
1021 cagtgatggt cagcctgctg actgattatt cacctcagct ccagaaacca aagttctgat
1081 aagcggccgc
```

FIG. 5A

```
hOTCLW5    --------------ATGCTGTTCAACCTGAGAATCCTGCTGAACAACGCCGCCTTCAGAA  46
hOTCLW6    --------------ATGCTGTTCAACCTGCGCATCCTGCTGAACAACGCCGCCTTCCGCA  46
hOTCco     --------------ATGCTGTTCAACCTGCGAATCCTGCTGAACAATGCCGCTTTTCGGA  46
LW3        CTGCAGCCGCCACCATGCTGTTCAACCTGCGAATCCTGCTGAACAACGCCGCTTTTCGGA  60
LW4        CTGCAGCCGCCACCATGCTGTTCAACCTGCGAATCCTGCTGAACAACGCCGCTTTTCGGA  60
hOTwt      --------------ATGCTGTTTAATCTGAGGATCCTGTTAAACAATGCAGCTTTTAGAA  46
                         ******  *** * ****** * ***    * * hOTCLW5    ACGGCCACAACTTCATGGTGAGAAACTTCAGATGCGGCCAGCCCCTGCAGAACAAGGTGC  106
hOTCLW6    ACGGCCACAACTTCATGGTGCGCAACTTCCGCTGCGGCCAGCCCCTGCAGAACAAGGTGC  106
hOTCco     ACGGGCACAATTTCATGGTGAGGAACTTTCGCTGCGGACAGCCCCTCCAGAACAAGGTCC  106
LW3        ACGGGCACAACTTTATGGTGAGGAACTTTCGCTGCGGACAGCCCCTCCAGAATAAGGTCC  120
LW4        ACGGGCACAACTTTATGGTGAGGAACTTTCGCTGCGGACAGCCCCTCCAGAATAAGGTCC  120
hOTwt      ATGGTCACAACTTCATGGTTCGAAATTTTCGGTGTGGACAACCACTACAAAATAAAGTGC  106
           *  *  *****   *    *          * hOTCLW5    AGCTGAAGGGCAGAGACCTGCTGACCCTGAAGAACTTCACCGGCGAGGAGATCAAGTACA  166
hOTCLW6    AGCTGAAGGGCCGCGACCTGCTGACCCTGAAGAACTTCACCGGCGAGGAGATCAAGTACA  166
hOTCco     AGCTGAAGGGCAGGGACCTGCTGACCCTGAAAAATTTCACAGGGGAGGAAATCAAGTACA  166
LW3        AGCTGAAGGGCAGGGACCTGCTGACCCTGAAAAATTTCACAGGGGAGGAAATCAAGTATA  180
LW4        AGCTGAAGGGCAGGGACCTGCTGACCCTGAAAAATTTCACAGGGGAGGAAATCAAGTATA  180
hOTwt      AGCTGAAGGGCCGTGACCTTCTCACTCTAAAAAACTTTACCGGAGAAGAAATTAAATATA  166
           ***********    * *****  *   ** *         * hOTCLW5    TGCTGTGGCTGAGCGCCGACCTGAAGTTCAGAATCAAGCAGAAGGGCGAGTACCTGCCCC  226
hOTCLW6    TGCTGTGGCTGAGCGCCGACCTGAAGTTCCGCATCAAGCAGAAGGGCGAGTACCTGCCCC  226
hOTCco     TGCTGTGGCTGTCAGCCGATCTGAAGTTCCGGATCAAGCAGAAGGGCGAATATCTGCCTC  226
LW3        TGCTGTGGCTGTCAGCTGATCTGAAGTTCCGGATCAAGCAGAAGGGCGAATATCTGCCTC  240
LW4        TGCTGTGGCTGTCAGCTGATCTGAAGTTCCGGATCAAGCAGAAGGGCGAATATCTGCCTC  240
hOTwt      TGCTATGGCTATCAGCAGATCTGAAATTTAGGATAAAACAGAAGGAGAGTATTTGCCTT  226
           ** *       ***    *  *    **** hOTCLW5    TGCTGCAGGGCAAGAGCCTGGGCATGATCTTCGAGAAGAGAAGCACCAGAACCAGACTGA  286
hOTCLW6    TGCTGCAGGGCAAGAGCCTGGGCATGATCTTCGAGAAGCGCAGCACCCGCACCCGCCTGA  286
hOTCco     TGCTCCAGGGCAAGAGCCTGGGGATGATCTTCGAAAAGCGCAGTACTCGGACCAGACTGT  286
LW3        TGCTCCAGGGCAAAAGCCTGGGGATGATCTTCGAAAAGCGCAGTACTCGGACCAGACTGT  300
LW4        TGCTCCAGGGCAAAAGCCTGGGGATGATCTTCGAAAAGCGCAGTACTCGGACCAGACTGT  300
hOTwt      TATTGCAAGGGAAGTCCTTAGGCATGATTTTTGAGAAAAGAAGTACTCGAACAAGATTGT  286
              *       *    ***     *   * ** * ** hOTCLW5    GCACCGAGACCGGCCTGGCCCTGCTGGGCGGCCACCCCTGCTTCCTGACCACCCAGGACA  346
hOTCLW6    GCACCGAGACCGGCCTGGCCCTGCTGGGCGGCCACCCCTGCTTCCTGACCACCCAGGACA  346
hOTCco     CAACAGAGACTGGATTCGCACTGCTGGGAGGACACCCATGTTTTCTGACCACACAGGACA  346
LW3        CAACCGAGACTGGATTCGCTCTGCTGGGAGGACACCCTTGTTTTCTGACCACTCAGGACA  360
LW4        CAACCGAGACTGGATTCGCTCTGCTGGGAGGACACCCTTGTTTTCTGACCACTCAGGACA  360
hOTwt      CTACAGAAACAGGCTTTGCACTTCTGGGAGGACATCCTTGTTTTCTTACCACACAAGATA  346
                *  *   *    ** * *  *   **   * hOTCLW5    TCCACCTGGGCGTGAACGAGAGCCTGACCGACACCGCCAGAGTGCTGAGCAGCATGGCCG  406
hOTCLW6    TCCACCTGGGCGTGAACGAGAGCCTGACCGACACCGCCCGCGTGCTGAGCAGCATGGCCG  406
hOTCco     TTCATCTGGGAGTGAACGAGTCCCTGACCGACACAGCACGCGTCCTGAGCTCCATGGCTG  406
LW3        TTCACCTGGGAGTGAACGAGTCCCTGACCGACACTGCTCGCGTCCTGAGCTCTATGGCCG  420
LW4        TTCACCTGGGAGTGAACGAGTCCCTGACCGACACTGCTCGCGTCCTGAGCTCTATGGCCG  420
hOTwt      TTCATTTGGGTGTGAATGAAAGTCTCACGGACACGGCCCGTGTATTGTCTAGCATGGCAG  406
           * **  ****  **** **    ** ** *****  *    **  **  *   *****  
```

FIG. 5B

```
hOTCLW5    ACGCCGTGCTGGCCAGAGTGTACAAGCAGAGCGACCTGGACACCCTGGCCAAGGAGGCCA 466
hOTCLW6    ACGCCGTGCTGGCCCGCGTGTACAAGCAGAGCGACCTGGACACCCTGGCCAAGGAGGCCA 466
hOTCco     ATGCAGTGCTGGCTCGAGTCTACAAACAGTCTGACCTGGATACCCTGGCCAAGGAAGCTT 466
LW3        ACGCTGTGCTAGCTCGAGTCTACAAACAGTCCGACCTGGATACCCTGGCCAAGGAAGCTT 480
LW4        ACGCTGTGCTGGCTCGAGTCTACAAACAGTCCGACCTGGATACCCTGGCCAAGGAAGCTT 480
hOTwt      ATGCAGTATTGGCTCGAGTGTATAAACAATCAGATTTGGACACCCTGGCTAAAGAAGCAT 466
           *     *  * **   *             **** hOTCLW5    GCATCCCCATCATCAACGGCCTGAGCGACCTGTACCACCCCATCCAGATCCTGGCCGACT 526
hOTCLW6    GCATCCCCATCATCAACGGCCTGAGCGACCTGTACCACCCCATCCAGATCCTGGCCGACT 526
hOTCco     CTATCCCAATCATTAATGGCCTGAGTGACCTGTATCACCCCATCCAGATTCTGGCCGATT 526
LW3        CTATCCCAATTATTAACGGCCTGTCAGACCTGTATCACCCCATCCAGATTCTGGCCGATT 540
LW4        CTATCCCAATTATTAACGGCCTGTCAGACCTGTATCACCCCATCCAGATTCTGGCCGATT 540
hOTwt      CCATCCCAATTATCAATGGGCTGTCAGATTTGTACCATCCTATCCAGATCCTGGCTGATT 526
             ***     *          **** *  * hOTCLW5    ACCTGACCCTGCAGGAGCACTACAGCAGCCTGAAGGGCCTGACCCTGAGCTGGATCGGCG 586
hOTCLW6    ACCTGACCCTGCAGGAGCACTACAGCAGCCTGAAGGGCCTGACCCTGAGCTGGATCGGCG 586
hOTCco     ACCTGACCCTCCAGGAGCATTATTCTAGTCTGAAAGGGCTGACACTGAGCTGGATTGGGG 586
LW3        ACCTGACCCTCCAGGAGCACTATTCTAGTCTGAAAGGGCTGACACTGAGTTGGATTGGGG 600
LW4        ACCTGACCCTCCAGGAGCACTATTCTAGTCTGAAAGGGCTGACACTGAGTTGGATTGGGG 600
hOTwt      ACCTCACGCTCCAGGAACACTATAGCTCTCTGAAAGGTCTTACCCTCAGCTGGATCGGGG 586
           **   *          ***       ***  * hOTCLW5    ACGGCAACAACATCCTGCACAGCATCATGATGAGCGCCGCCAAGTTCGGCATGCACCTGC 646
hOTCLW6    ACGGCAACAACATCCTGCACAGCATCATGATGAGCGCCGCCAAGTTCGGCATGCACCTGC 646
hOTCco     ACGGAAACAATATCCTGCACTCCATTATGATGAGCGCCGCCAAGTTTGGAATGCACCTCC 646
LW3        ACGGAAACAATATCCTGCACTCTATTATGATGTCAGCCGCCAAGTTTGGAATGCACCTCC 660
LW4        ACGGAAACAATATCCTGCACTCTATTATGATGTCAGCCGCCAAGTTTGGAATGCACCTCC 660
hOTwt      ATGGGAACAATATCCTGCACTCCATCATGATGAGCGCAGCGAAATTCGGAATGCACCTTC 646
           *  * *****    ****        ******** * hOTCLW5    AGGCCGCCACCCCCAAGGGCTACGAGCCCGACGCCAGCGTGACCAAGCTGGCCGAGCAGT 706
hOTCLW6    AGGCCGCCACCCCCAAGGGCTACGAGCCCGACGCCAGCGTGACCAAGCTGGCCGAGCAGT 706
hOTCco     AGGCTGCAACCCCAAAAGGCTACGAACCCGATGCCTCCGTGACAAAGCTGGCAGAACAGT 706
LW3        AGGCTGCAACCCCAAAAGGCTACGAACCCGATGCCTCAGTGACAAAGCTGGCTGAACAGT 720
LW4        AGGCTGCAACCCCAAAAGGCTACGAACCCGATGCCTCAGTGACAAAGCTGGCTGAACAGT 720
hOTwt      AGGCAGCTACTCCAAAGGGTTATGAGCCGGATGCTAGTGTAACCAAGTTGGCAGAGCAGT 706
           **                   *   ** hOTCLW5    ACGCCAAGGAGAACGGCACCAAGCTGCTGCTGACCAACGACCCCCTGGAGGCCGCCCACG 766
hOTCLW6    ACGCCAAGGAGAACGGCACCAAGCTGCTGCTGACCAACGACCCCCTGGAGGCCGCCCACG 766
hOTCco     ATGCCAAAGAGAACGGCACTAAGCTGCTGCTGACCAATGACCCTCTGGAGGCCGCTCACG 766
LW3        ACGCCAAAGAGAACGGCACTAAGCTGCTGCTGACCAACGACCCTCTGGAGGCCGCTCACG 780
LW4        ACGCCAAAGAGAACGGCACTAAGCTGCTGCTGACCAACGACCCTCTGGAGGCCGCTCACG 780
hOTwt      ATGCCAAAGAGAATGGTACCAAGCTGTTGCTGACAAATGATCCATTGGAAGCAGCGCATG 766
           * *** *   **  ***      ** * hOTCLW5    GCGGCAACGTGCTGATCACCGACACCTGGATCAGCATGGGCCAGGAGGAGGAGAAGAAGA 826
hOTCLW6    GCGGCAACGTGCTGATCACCGACACCTGGATCAGCATGGGCCAGGAGGAGGAGAAGAAGA 826
hOTCco     GAGGCAACGTGCTGATCACTGATACCTGGATTAGTATGGGACAGGAGGAAGAGAAGAAGA 826
LW3        GAGGCAACGTGCTGATCACCGATACCTGGATTAGTATGGGACAGGAGGAAGAGAAGAAGA 840
LW4        GAGGCAACGTGCTGATCACCGATACCTGGATTAGTATGGGACAGGAGGAAGAGAAGAAGA 840
hOTwt      GAGGCAATGTATTAATTACAGACACTTGGATAAGCATGGGACAAGAAGAGGAGAAGAAA  826
           * ***** **   *  * ** ** ** ** ***** ** *****  ** ** ** ** ******** *
```

FIG. 5C

```
hOTCLW5    AGAGACTGCAGGCCTTCCAGGGCTACCAGGTGACCATGAAGACCGCCAAGGTGGCCGCCA 886
hOTCLW6    AGCGCCTGCAGGCCTTCCAGGGCTACCAGGTGACCATGAAGACCGCCAAGGTGGCCGCCA 886
hOTCco     AGCGGCTCCAGGCCTTCCAGGGCTACCAGGTGACAATGAAAACTGCTAAGGTCGCAGCCA 886
LW3        AGCGGCTCCAGGCCTTCCAGGGCTACCAGGTGACAATGAAAACCGCTAAGGTCGCAGCCA 900
LW4        AGCGGCTCCAGGCCTTCCAGGGCTACCAGGTGACAATGAAAACCGCTAAGGTCGCAGCCA 900
hOTwt      AGCGGCTCCAGGCTTTCCAAGGTTACCAGGTTACAATGAAGACTGCTAAAGTTGCTGCCT 886
           ** *  * *  ******  ***      *** hOTCLW5    GCGACTGGACCTTCCTGCACTGCCTGCCCAGAAAGCCCGAGGAGGTGGACGACGAGGTGT 946
hOTCLW6    GCGACTGGACCTTCCTGCACTGCCTGCCCCGCAAGCCCGAGGAGGTGGACGACGAGGTGT 946
hOTCco     GCGACTGGACCTTTCTGCATTGCCTGCCCAGAAAGCCTGAAGAGGTGGACGATGAGGTCT 946
LW3        GCGATTGGACCTTTCTGCACTGCCTGCCCAGAAAGCCCGAAGAGGTGGACGACGAGGTCT 960
LW4        GCGATTGGACCTTTCTGCACTGCCTGCCCAGAAAGCCCGAAGAGGTGGACGACGAGGTCT 960
hOTwt      CTGACTGGACATTTTTACACTGCTTGCCCAGAAAGCCAGAAGAAGTGGATGATGAAGTCT 946
            *   *  * ***** * ***   *    * hOTCLW5    TCTACAGCCCCAGAAGCCTGGTGTTCCCCGAGGCCGAGAACAGAAAGTGGACCATCATGG 1006
hOTCLW6    TCTACAGCCCCCGCAGCCTGGTGTTCCCCGAGGCCGAGAACCGCAAGTGGACCATCATGG 1006
hOTCco     TCTACTCACCCAGAAGCCTGGTGTTTCCTGAAGCTGAGAATAGGAAGTGGACAATCATGG 1006
LW3        TCTACTCTCCCAGAAGCCTGGTGTTTCCCGAAGCTGAGAATAGGAAGTGGACAATTATGG 1020
LW4        TCTACTCTCCCAGAAGCCTGGTGTTTCCCGAAGCTGAGAATAGGAAGTGGACAATTATGG 1020
hOTwt      TTTATTCTCCTCGATCACTAGTGTTCCCAGAGGCAGAAAACAGAAAGTGGACAATCATGG 1006
           *         *      *    ** *  * ******  **** hOTCLW5    CCGTGATGGTGAGCCTGCTGACCGACTACAGCCCCCAGCTGCAGAAGCCCAAGTTCTGA- 1065
hOTCLW6    CCGTGATGGTGAGCCTGCTGACCGACTACAGCCCCCAGCTGCAGAAGCCCAAGTTCTGA- 1065
hOTCco     CAGTGATGGTCAGCCTGCTGACTGATTATTCCCTCAGCTCCAGAAACCAAAGTTCTGAT 1066
LW3        CAGTGATGGTCAGCCTGCTGACTGATTATTCACCTCAGCTCCAGAAACCAAAGTTCTGAT 1080
LW4        CAGTGATGGTCAGCCTGCTGACTGATTATTCACCTCAGCTCCAGAAACCAAAGTTCTGAT 1080
hOTwt      CTGTCATGGTGTCCCTGCTGACAGATTACTCACCTCAGCTCCAGAAGCCTAAATTT---- 1062
           *  *  *****       *** * hOTCLW5    ----------
hOTCLW6    ----------
hOTCco     AA-------- 1068
LW3        AAGCGGCCGC 1090
LW4        AAGCGGCCGC 1090
hOTwt      ----------
```

COMPOSITIONS USEFUL IN TREATMENT OF ORNITHINE TRANSCARBAMYLASE (OTC) DEFICIENCY

CROSS-REFERENCE TO RELATED APPLICATIONS

This is a 371 national stage of PCT/US2015/019536, filed Mar. 9, 2015, which claims the benefit under 35 USC 119(e) of U.S. Provisional Patent Application No. 61/950,157, filed Mar. 9, 2014.

STATEMENT REGARDING FEDERALLY SPONSORED RESEARCH OR DEVELOPMENT

This work was supported in part by grants from the National Institutes of Health, Nos. P01-HD057247, P01-HL059407, and P30-DK047757. The US government may have certain rights in this invention.

INCORPORATION-BY-REFERENCE OF MATERIAL SUBMITTED IN ELECTRONIC FORM

Applicant hereby incorporates by reference the Sequence Listing material filed in electronic form herewith. This file is labeled "UPN-14-7037APCT_ST25.txt".

BACKGROUND OF THE INVENTION

Ornithine transcarbamylase (OTC) deficiency accounts for nearly half of all cases of inborn errors of urea synthesis, with a prevalence estimated to be at least 1 in 15,000. Urea cycle defects put patients at risk of life threatening elevation of ammonia that can lead to irreversible cognitive impairment, coma and death. Newborn males with complete deficiency develop hyperammonemic coma within the first 3 days of life, which if untreated, is lethal.

Current therapies for OTC deficiency (OTCD) have numerous challenges. Patients can be managed with a low protein diet in combination with the use of medications that activate alternate nitrogen clearance pathways, but this does not prevent hyperammonemic crises. Despite the use of dialysis and alternate pathway therapy, there is almost a 50% mortality rate in neonates. Liver transplantation can cure OTCD, but donor liver is limiting, the procedure carries significant morbidity and immunosuppressive drugs are necessary for the duration of the subject's life.

Gene therapy of a metabolic disease such as OTCD presents a more challenging model for gene replacement therapy than other conditions. Because the gene acts in a cell-autonomous manner (i.e., it can only influence the cell in which it is expressed), therapeutic effects should be directly correlated with the number of target cells that are transduced, rather than with the net level of expression in liver such as with a secreted protein where high expression per cell can overcome low transduction. Furthermore, there has been at least one published report that hOTCwt mRNA is unstable. [Wang, L., et al, Molecular Genetics and Metabolism, 105 (2012) 203-211].

There have been published reports of using viral vectors to try to treat OTC deficiency. For example, several groups have tried this in murine models of OTC deficiency, using recombinant adenoviruses carrying rat, mouse, or human OTC cDNA. Some measure of successful reconstitution of liver OTC activity and correction of metabolic derangements have been reported in animal models with viruses carrying rat or mouse OTC cDNA. Previous studies using adenoviral vectors have illustrated the difficulties of expressing sufficient levels of active human OTC in OTCD mice.

Therefore, there is a need for other approaches to OTCD therapy.

SUMMARY OF THE INVENTION

In one aspect, a composition comprising a non-viral carrier and an engineered hOTC is provided which is less than 80% identical to the wild-type hOTC sequence over the full-length hOTC of the wild-type sequence (e.g., SEQ ID NO:1), or a fragment thereof which comprises the mature hOTC but lacking at least the native leader sequence, or another intermediate which comprises at least the mature hOTC and expresses a functional hOTCase. Suitably, the engineered sequence has been preferably codon optimized and further improved such that it enhances at least one of transduction, transcription and/or translation of the enzyme. The composition comprises a nucleic acid molecule comprising an engineered sequence encoding human ornithine transcarbamylase (hOTCase) and expression control sequences which direct expression of hOTCase in a liver cell, wherein the hOTC nucleic acid sequence is less than 80% identical to the wild-type hOTC sequence over at least the mature hOTC sequence of SEQ ID NO:1, wherein said hOTC nucleic acid sequence is selected from the nucleic acid sequence comprising SEQ ID NO: 5 or a nucleic acid sequence at least about 96 to about 99% identical thereto, a nucleic acid sequence selected from SEQ ID NO: 9, or a nucleic acid sequence at least about 96 to about 99% identical thereto, a nucleic acid sequence comprising SEQ ID NO: 11 or a nucleic acid sequence at least about 96 to about 99% identical thereto, or a nucleic acid sequence comprising SEQ ID NO: 13 or a nucleic acid sequence at least about 96 to about 99% identical thereto. In one embodiment, the hOTC is a chimeric OTC which comprises a heterologous transit sequence substituted for the native transit sequence of SEQ ID NO: 5, 6, 7, 8, 9, 10, 11, 12 or 13.

In one aspect, the composition comprises a plasmid. In one example, the plasmid has the sequence of SEQ ID NO: 6.

In another aspect, the engineered hOTC nucleic acid molecule is formulated in a moiety selected from the group consisting of micelles, liposomes, cationic lipid-nucleic acid compositions, poly-glycan compositions, block copolymers and other polymers, lipid and/or cholesterol-based-nucleic acid conjugates. In a further aspect, a pharmaceutical composition comprises an excipient and an effective amount of the engineered hOTC nucleic acid molecule.

In still another aspect, a composition is provided which comprises the engineered hOTC nucleic acid molecule for use in a method of treatment of a disease or medical condition associated with ornithine transcarbamylase deficiency in a human patient. In a further embodiment, a composition comprises a nucleic acid molecule encoding functional human ornithine transcarbamylase for use in a method in preventing and/or treating fibrosis or cirrhosis in a subject heterozygous for ornithine transcarbamylase deficiency in a human patient. In yet another embodiment, a composition comprises a nucleic acid molecule comprising a nucleic acid sequence encoding functional human ornithine transcarbamylase for use in a method for preventing and/or treating hepatocellular carcinoma in a subject heterozygous for ornithine transcarbamylase deficiency.

In still another embodiment, a method for delivering ornithine transcarbamylase to a subject in need thereof and/or for treating ornithine transcarbamylase deficiency in a subject comprising delivering to a subject in need thereof the composition containing an engineered hOTC as described herein.

In still another aspect, a composition comprises an mRNA according to any one of SEQ ID NO: 10, 11, or 12 in a method for delivering ornithine transcarbamylase to a human patient in acute crisis. A composition as defined herein may also be used in a method for delivering ornithine transcarbamylase to a human patient following treatment of said patient with RNA.

In another aspect, a method for preventing and/or treating fibrosis or cirrhosis in a subject heterozygous for ornithine transcarbamylase deficiency is provided, which method comprises delivering to a subject a composition comprising a nucleic acid sequence encoding functional human ornithine transcarbamylase.

A method for preventing and/or treating hepatocellular carcinoma in a subject heterozygous for ornithine transcarbamylase deficiency is provide. This method comprises delivering a composition comprising a nucleic acid sequence encoding functional human ornithine transcarbamylase.

Other aspects and advantages of the invention will be readily apparent from the following detailed description of the invention.

BRIEF DESCRIPTION OF THE DRAWINGS

FIG. 1A provides a wild-type hOTC cDNA, which has 324 A, 223 C, 246 G, and 269 T [SEQ ID NO: 1].

FIG. 1B-1C provides the human ornithine transcarbamylase sequence encoded by the sequence of FIG. 1A [SEQ ID NO:2].

FIG. 2 provides an engineered hOTC cDNA, with an altered GC ratio. The base count in the sequence is 283 A, 285 C, 284 G, and 216 T [SEQ ID NO: 3].

FIG. 3 provides an engineered hOTC cDNA termed LW3 [SEQ ID NO:4]. The base count in this sequence is 279 A, 303 C, 288 G, and 220 T. The start codon for the hOTC open reading frame (ORF) is preceded by a Kozak sequence in this figure. The coding sequence for the leader begins at nucleotide 15 (first 96 nucleotides), followed by the coding sequence for the 322 amino acid hOTCase. In this figure the stop codon is followed by a NotI restriction site (GCGGC-CGC) which is a remnant of the vector.

FIG. 4 provides an engineered hOTC cDNA termed LW4 [SEQ ID NO:5]. The base count in this sequence is 278 A, 303 C, 289 G, and 220 T. The coding sequence for the leader begins at nucleotide 15 (first 96 nucleotides), followed by the coding sequence for the 322 amino acid hOTCase. In this figure the stop codon is followed by a NotI restriction site (GCGGCCGC) which is a remnant of the vector.

FIGS. 5A-5C provides an alignment of the cDNA sequences of the wild-type hOTC, and five engineered sequences, GS [SEQ ID NO: 3], LW3 [SEQ ID NO:4], LW4 [SEQ ID NO: 5], LW5 [SEQ ID NO: 8] and LW6 [SEQ ID NO:9]. The aligned sequences contain a Kozak sequence (first 14 nucleotides of LW3 and LW4) and a restriction enzyme site (following termination codon for LW3 and LW4), which are not part of the open reading frame.

DETAILED DESCRIPTION OF THE INVENTION

An engineered human (h) ornithine transcarbamylase (OTC) cDNA is provided herein, which was designed to maximize translation and improve mRNA stability as compared to the wild-type hOTC DNA and/or mRNA. Also provided herein are engineered hOTC mRNA sequences. These compositions may be used in therapeutic and/or prophylactic methods as described herein. Optionally, these compositions are used in combination other therapies consistent with the standard of care for the conditions for which the subject (e.g., a human subject) has been diagnosed.

For comparison purposes, a wild-type human OTC cDNA sequence is illustrated in FIG. 1A. This sequence encodes the human ornithine transcarbamylase of the amino acid sequence of FIGS. 1A-1C. This same amino acid sequence is encoded by the engineered hOTC genes of FIGS. 2A-FIG. 5. The hOTC enzyme, which may be referred to as hOTCase to distinguish from the gene, is expressed from this sequence in the form of a pre-protein having a 32 amino acid leader peptide at its N-terminus (encoded by nt 1-96 of FIG. 1, about amino acids 1 to about 32 of SEQ ID NO: 2) which is cleaved after directing the enzyme to the cellular mitochondria, leaving the 322 amino acid residue "mature" protein (about amino acid 33 to about amino acid 354 of SEQ ID NO: 2. This "so-called mature" hOTCase is a homotrimeric protein with a 322 amino acid residue sequence in each polypeptide chain. Optionally, as an alternative to the wild-type sequence of SEQ ID NO:2, one may select a sequence which includes one or more of the naturally occurring polymorphic positions that are not involved in disease: F101, L111, WI193-194 of SEQ ID NO: 2 (see, e.g., www.uniprot.org/uniprot/P00480).

Although all of the engineered cDNA sequences are about 77% to about 78% identical to the wt hOTC nucleic acid sequence of FIG. 1A [SEQ ID NO:1], there are structural differences between these sequences (see alignment in FIG. 5 illustrating same). Particularly, there is about 4% difference in nucleic acid sequences between hOTCco of FIG. 2 [SEQ ID NO: 3] and the hOTCcoLW4 of FIG. 4 [SEQ ID NO:5]. There is only one nt difference between LW-3 [FIG. 3, SEQ ID NO: 4] and LW-4 [FIG. 4, SEQ ID NO: 5], i.e., 0.094% (1/1062) difference (an A in LW-3 is changed to a G in LW-4 as shown in FIG. 5].

In one embodiment, a modified hOTC coding sequence is provided which sequence has less than about 80% identity, preferably about 77% identity or less to the full-length wild-type hOTC coding sequence (FIG. 1A, SEQ ID NO:1), which encodes functional hOTCase. In one embodiment, the modified hOTC coding sequence is characterized by improved stability as compared to wt hOTC following AAV-mediated delivery (e.g., rAAV). Additionally or alternatively, a modified hOTC coding sequence is provided which lacks alternative reading frames for proteins of at least about 9 amino acids in length. Additionally, or alternatively, a modified hOTC coding sequence is provided which has hOTCase expression levels at least about 25 fold, at least about 50 fold, or at least about 100-fold when measured following expression from a viral vector, as compared to the hOTCase wild-type. Additionally, or alternatively, a modified hOTC coding sequence is provided which has hOTCase liver activity which is at least about 10-fold higher, at least about 20-fold higher, or at least about 30-fold higher as compared to the hOTCase wild-type expressed from a viral vector.

In one embodiment, a modified hOTC coding sequence is 96% to 99.9% identical to the sequence encoding the mature enzyme (about nt 99 to about 1068) or full-length of FIG. 4 (hOTCco-LW4, SEQ ID NO: 5), or 96.5% to 99% identical, or about 97%, or about 98% identical to SEQ ID NO:5 (FIG. 4).

In one embodiment, a modified hOTC coding sequence is 96% to 99.9% identical to the sequence encoding the mature enzyme (about nt 99 to about 1068) of FIG. 3 (hOTCco-LW3, SEQ ID NO:4), or 96.5% to 99% identical, or about 97%, or about 98% identical to SEQ ID NO: 4 (FIG. 3).

In another embodiment, a modified hOTC coding sequence is 96% to 99.9% identical to the sequence encoding the mature enzyme (about nt 99 to about 1068) or the full-length of FIG. 2 (hOTCco, SEQ ID NO:3), or 96.5% to 99% identical, or about 97%, or 98% identical to SEQ ID NO: 3 (FIG. 2).

In still another embodiment, a modified hOTC coding sequence has the sequence encoding the mature protein (about nt 99 to about 1068) or the full-length of hOTCco-LW5 [SEQ ID NO: 8] or hOTCco-LW6 [SEQ ID NO:9], or a sequence 96% to 99.9% identical thereto. hOTCco-LW5 and hOTCco-LW6 are about 97% identical to each other, and each is about 78% identical to the wild-type sequence [SEQ ID NO: 1].

The sequences of FIGS. 2-5 are provided as the sense strand of the cDNA sequences. The present invention also encompasses the anti-sense strands corresponding to these cDNA sequences and corresponding RNA, e.g., mRNA, sequences. For example, the engineered mRNA of SEQ ID NO: 10, corresponds to the DNA of SEQ ID NO:4; the engineered RNA of SEQ ID NO: 11, corresponds to the DNA of SEQ ID NO: 5; the engineered RNA of SEQ ID NO: 12, corresponds to the DNA of SEQ ID NO: 8; and the RNA of SEQ ID NO: 13 corresponds to the DNA of SEQ ID NO:9. These RNA sequences, and sequences which are 95% to 99%, or about 97%, or about 98% identical to one or more of these sequences are encompassed within the scope of this invention. Methods for aligning and determining RNA identity are known in the art and include published and publically available web-based or commercially available databases and services. See, e.g., LocARNA, CARNA, as well as other programs identified elsewhere therein.

In one embodiment of the invention, the mRNA sequence may be delivered using a selected RNA delivery system, examples of which are supplied herein.

Also encompassed herein are fragments, e.g., the sequences encoding the transit peptide (amino acids 1 to about 32), about amino acids 332 to about 354, an intermediate hOTC enzyme, or the mature enzyme, or other fragments as may be desired. Reference may be made to SEQ ID NO:2. See, e.g., Ye et al. 2001, Hum Gene Ther 12: 1035-1046.

In another embodiment, a chimeric OTC is provided in which the N-terminal presequence of wild-type OTC is replaced with a transit sequence from another source which is compatible with the subject's system such that it effectively transports the mature hOTCase encoded by the chimeric OTC gene to the desired organelle. See, e.g., Ye et al. 2001, Hum Gene Ther 12: 1035-1046. Such transit sequences encode a transit peptide (also termed a signal peptide, targeting signal, or localization signal) which is fused to the coding sequence for the mature hOTC of SEQ ID NO: 1, 3, 4, 5, 8 and/or 9. For example, the wild-type hOTC transit sequence corresponds to about the first 98 nucleotides of SEQ ID NO: 1. To construct a chimeric OTC, these wild-type N-terminal sequences may be removed (about nucleic acids 1 to about nt 96-nt 98) and replaced with a heterologous transit sequence. Suitable transit peptides are preferably, although not necessarily of human origin. Suitable transit peptides may be chosen from proline.bic.nus.edu.sg/spdb/zhang270.htm, which is incorporated by reference herein, or may be determined using a variety of computational programs for determining the transit peptide in a selected protein. Although not limited, such sequences may be from about 15 to about 50 amino acids in length, or about 20 to about 28 amino acids in length, or may be larger or smaller as required.

The term "percent (%) identity", "sequence identity", "percent sequence identity", or "percent identical" in the context of nucleic acid sequences refers to the residues in the two sequences which are the same when aligned for correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired.

Percent identity may be readily determined for amino acid sequences over the full-length of a protein, polypeptide, about 32 amino acids, about 330 amino acids, or a peptide fragment thereof or the corresponding nucleic acid sequence coding sequences. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence.

Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

Multiple sequence alignment programs are also available for nucleic acid sequences. Examples of such programs include, "Clustal W", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference.

In one embodiment, the modified hOTC genes described herein are engineered into a suitable genetic element (vector) useful for generating viral vectors and/or for delivery to a host cell, e.g., naked DNA, phage, transposon, cosmid, episome, etc., which transfers the hOTC sequences carried thereon. The selected vector may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y.

As used herein, an "expression cassette" refers to a nucleic acid molecule which comprises the hOTC sequences, promoter, and may include other regulatory sequences therefor, which cassette may be packaged into the capsid of a viral vector (e.g., a viral particle). Typically, such an expression cassette for generating a viral vector contains the hOTC sequences described herein flanked by packaging signals of the viral genome and other expression control sequences such as those described herein. For example, for an AAV viral vector, the packaging signals are the 5' inverted terminal repeat (ITR) and the 3' ITR.

In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting vector may be termed pseudotyped.

Typically, an expression cassette for an AAV vector comprises an AAV 5' ITR, the hOTC coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used.

In one embodiment, the construct is a DNA molecule (e.g., a plasmid) useful for generating viral vectors. An illustrative plasmid containing desirable vector elements is illustrated by pAAVsc.TBG.hOTCco-LW4, the sequence of which is SEQ ID NO: 6 and which is incorporated by reference. This illustrative plasmid contains an expression cassette comprising: scITR (nt 5-109 of SEQ ID NO: 6), a TATA signal (nt 851-854 of SEQ ID NO:6), a synthetic hOTC coding sequence (nt 976-2037 of SEQ ID NO: 6), a poly A (nt 2182-2046 on the complement of SEQ ID NO: 6), a scITR (nt 2378-2211 on the complement of SEQ ID NO: 6), and a liver specific (TBG) promoter (nt 4172-4760) of SEQ ID NO: 6). Other expression cassettes may be generated using the other synthetic hOTC coding sequences, and other expression control elements, described herein.

The abbreviation "sc" in this context refers to self-complementary. "Self-complementary AAV" refers a construct in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

The expression cassette typically contains a promoter sequence as part of the expression control sequences, e.g., located between the selected 5' ITR sequence and the hOTC coding sequence. The illustrative plasmid and vector described herein uses the liver-specific promoter thyroxin binding globulin (TBG). Alternatively, other liverspecific promoters may be used [see, e.g., The Liver Specific Gene Promoter Database, Cold Spring Harbor, rulai.schl.edu/LSPD/, such as, e.g., alpha 1 antitrypsin (A1AT); human albumin Miyatake et al., J. Virol., 71:5124 32 (1997), humAlb; and hepatitis B virus core promoter, Sandig et al., Gene Ther., 3:1002 9 (1996)]. TTR minimal enhancer/promoter, alpha-antitrypsin promoter, LSP (845 nt) 25 (requires intronless scAAV); or LSP1. Although less desired, other promoters, such as constitutive promoters, regulatable promoters [see, e.g., WO 2011/126808 and WO 2013/04943], or a promoter responsive to physiologic cues may be used in the vectors described herein.

In addition to a promoter, an expression cassette and/or a vector may contain one or more other appropriate transcription initiation, termination, enhancer sequences, efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. Examples of suitable polyA sequences include, e.g., SV40, SV50, bovine growth hormone (bGH), human growth hormone, and synthetic polyAs. Examples of suitable enhancers include, e.g., the alpha fetoprotein enhancer, the TTR minimal promoter/enhancer, LSP (TH-binding globulin promoter/alpha1-microglobulin/bikunin enhancer), amongst others. In one embodiment, the expression cassette comprises one or more expression enhancers. In one embodiment, the expression cassette contains two or more expression enhancers. These enhancers may be the same or may differ from one another. For example, an enhancer may include an Alpha mic/bik enhancer. This enhancer may be present in two copies which are located adjacent to one another. Alternatively, the dual copies of the enhancer may be separated by one or more sequences. In still another embodiment, the expression cassette further contains an intron, e.g, the Promega intron. Other suitable introns include those known in the art, e.g., such as are described in WO 2011/126808. Optionally, one or more sequences may be selected to stabilize mRNA. An example of such a sequence is a modified WPRE sequence, which may be engineered upstream of the polyA sequence and downstream of the coding sequence [see, e.g., M A Zanta-Boussif, et al, Gene Therapy (2009) 16: 605-619.

These control sequences are "operably linked" to the hOTC gene sequences. As used herein, the term "operably linked" refers to both expression control sequences that are contiguous with the gene of interest and expression control sequences that act in trans or at a distance to control the gene of interest.

Recombinant AAV viral vectors are well suited for delivery of the hOTC expression sequences described herein. Such AAV vectors may contain ITRs which are from the same AAV source as the capsid. Alternatively, the AAV ITRs may be from a different AAV source than that which supplies the capsid.

Where pseudotyped AAV is to be produced, the ITRs in the expression are selected from a source which differs from the AAV source of the capsid. For example, AAV2 ITRs may be selected for use with an AAV capsid having a particular efficiency for targeting liver (e.g., hepatocytes). AAV capsids may be selected from AAV8 [U.S. Pat. No. 7,790,449; U.S. Pat. No. 7,282,199] and rh10 [WO 2003/042397] for the compositions described herein. However, other AAV, including, e.g., AAV1, AAV2, AAV3, AAV4, AAV5, AAV6, AAV7, AAV9, and others such as, e.g., those described in WO 2003/042397; WO 2005/033321, WO 2006/110689; U.S. Pat. No. 7,588,772 B2, which are incorporated by reference herein] may be used in human subjects.

In one embodiment, a self-complementary AAV is provided. This viral vector may contain a Δ5' ITR and an AAV 3' ITR. In one example, the viral vector is scAAV2/8.TB-G.hOTCco. In another example, the viral vector is scAAV2/rh10.TBG.hOTCco. These vectors both contain the 5' ΔITR from AAV2, the liver-specific TBG promoter, an engineered hOTCco coding sequence of the invention, an SV40 polyA, and the 3' AAV2 ITR in an AAV8 capsid [see, e.g., U.S. Pat. No. 8,318,480B2] or AAV rh10 capsid. The sequence may be selected from engineered hOTC of one of SEQ ID NO: 3, 4, 5, 8 or 9. Optionally, the transit sequence of the engineered hOTC may be substituted with a heterologous transit sequence to provide a chimeric hOTC, which retains the mature hOTCase.

In another embodiment, a single-stranded AAV viral vector is provided. Such a vector may contain a 5' AAV ITR and a 3' ITR. One example is AAV2/8.TBG.hOTCco, which contains the full-length AAV2-5' ITR, the liver-specific TBG promoter, the hOTC coding sequence, a bovine growth hormone polyA, and AAV2-3' ITR. Another example is AAV2/8.TBG.hOTCco-.WPRE.bGH, which contains the same vector elements, and additionally contains the woodchuck hepatitis virus post-transcriptional regulatory element (WPRE). In other embodiments, WPRE is absent from constructs to be used in vivo. The engineered hOTC sequence (abbreviated herein hOTCco) may be selected from engineered hOTC of one of SEQ ID NO: 3, 4, 5, 8 or 9. Optionally, the transit peptide sequence of the engineered hOTC may be substituted with a heterologous transit sequence to provide a chimeric hOTC, which retains the mature hOTCase.

Still other promoters may be selected, including tissue specific promoters. Methods for generating and isolating AAV viral vectors suitable for delivery to a subject are known in the art. See, e.g. US Published Patent Application No. 2007/0036760 (Feb. 15, 2007), U.S. Pat. No. 7,790,449; U.S. Pat. No. 7,282,199; WO 2003/042397; WO 2005/033321, WO 2006/110689; and U.S. Pat. No. 7,588,772 B2]. The sequences of AAV8 and methods of generating vectors based on the AAV8 capsid are described in U.S. Pat. No. 7,282,199 B2, U.S. Pat. No. 7,790,449, and U.S. Pat. No. 8,318,480, which are incorporated herein by reference. In a one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level. In yet another system, the transgene flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065.

The available space for packaging may be conserved by combining more than one transcription unit into a single construct, thus reducing the amount of required regulatory sequence space. For example, a single promoter may direct expression of a single RNA that encodes two or three or more genes, and translation of the downstream genes are driven by IRES sequences. In another example, a single promoter may direct expression of an RNA that contains, in a single open reading frame (ORF), two or three or more genes separated from one another by sequences encoding a self-cleavage peptide (e.g., T2A) or a protease recognition site (e.g., furin). The ORF thus encodes a single polyprotein, which, either during (in the case of T2A) or after translation, is cleaved into the individual proteins (such as, e.g., transgene and dimerizable transcription factor). It should be noted, however, that although these IRES and polyprotein systems can be used to save AAV packaging space, they can only be used for expression of components that can be driven by the same promoter. In another alternative, the transgene capacity of AAV can be increased by providing AAV ITRs of two genomes that can anneal to form head to tail concatamers.

Optionally, the hOTC genes described herein may be used to generate viral vectors other than rAAV. Such other viral vectors may include any virus suitable for gene therapy may be used, including but not limited to adenovirus; herpes virus; lentivirus; retrovirus; etc. Suitably, where one of these other vectors is generated, it is produced as a replication-defective viral vector.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication. Such replication-defective viruses may be adeno-associated viruses (AAV), adenoviruses, lentiviruses (integrating or non-integrating), or another suitable virus source.

The pharmaceutical compositions described herein are designed for delivery to subjects in need thereof by any suitable route or a combination of different routes. Direct or intrahepatic delivery to the liver is desired and may optionally be performed via intravascular delivery, e.g., via the portal vein, hepatic vein, bile duct, or by transplant. Alternatively, other routes of administration may be selected (e.g., oral, inhalation, intranasal, intratracheal, intraarterial, intraocular, intravenous, intramuscular, and other parenteral routes). The hOTC delivery constructs described herein may be delivered in a single composition or multiple compositions. Optionally, two or more different AAV may be delivered [see, e.g., WO 2011/126808 and WO 2013/049493]. In another embodiment, such multiple viruses may contain different replication-defective viruses (e.g., AAV, adenovirus, and/or lentivirus). Alternatively, delivery may be mediated by non-viral constructs, e.g., "naked DNA", "naked plasmid DNA", RNA, and mRNA; coupled with various delivery compositions and nano particles, including, e.g., micelles, liposomes, cationic lipid-nucleic acid compositions, poly-glycan compositions and other polymers, lipid and/or cholesterol-based-nucleic acid conjugates, and other constructs such as are described herein. See, e.g., X. Su et al, Mol. Pharmaceutics, 2011, 8 (3), pp 774-787; web publication: Mar. 21, 2011; WO2013/182683, WO 2010/053572 and WO 2012/170930, both of which are incorporated herein by reference, Such non-viral hOTC delivery constructs may be administered by the routes described previously.

The viral vectors, or non-viral DNA or RNA transfer moieties, can be formulated with a physiologically acceptable carrier for use in gene transfer and gene therapy applications. In the case of AAV viral vectors, quantification of the genome copies ("GC") may be used as the measure of the dose contained in the formulation. Any method known in the art can be used to determine the genome copy (GC) number of the replication-defective virus compositions of the invention. One method for performing AAV GC number titration is as follows: Purified AAV vector samples are first treated with DNase to eliminate un-encapsidated AAV genome DNA or contaminating plasmid DNA from the production process. The DNase resistant particles are then subjected to heat treatment to release the genome from the capsid. The released genomes are then quantitated by real-time PCR using primer/probe sets targeting specific region of the viral genome (usually poly A signal). The replication-defective virus compositions can be formulated in dosage units to contain an amount of replication-defective virus that is in the range of about $1.0 \times 10^9$ GC to about $1.0 \times 10^{15}$ GC (to treat an average subject of 70 kg in body weight), and preferably $1.0 \times 10^{12}$ GC to $1.0 \times 10^{14}$ GC for a human patient. Preferably, the dose of replication-defective virus in the formulation is $1.0 \times 10^9$ GC, $5.0 \times 10^9$ GC, $1.0 \times 10^{10}$ GC, $5.0 \times 10^{10}$ GC, $1.0 \times 10^{11}$ GC, $5.0 \times 10^{11}$ GC, $1.0 \times 10^{12}$ GC, $5.0 \times 10^{12}$ GC, or $1.0 \times 10^{13}$ GC, $5.0 \times 10^{13}$ GC, $1.0 \times 10^{14}$ GC, $5.0 \times 10^{14}$ GC, or $1.0 \times 10^{15}$ GC.

DNA and RNA is generally measured in the nanogram (ng) to microgram (μg) amounts of the nucleic acids. In general, for a treatment in a human preferably dosages of the RNA in the range of 1 ng to 700 μg, 1 ng to 500 μg, 1 ng to 300 μg, 1 ng to 200 μg, or 1 ng to 100 μg are formulated and administered. Similar dosage amounts of a DNA molecule containing an expression cassette and not delivered to a subject via a viral vector may be utilized for non-viral hOTC DNA delivery constructs.

Production of lentivirus is measured as described herein and expressed as IU per volume (e.g., mL). IU is infectious unit, or alternatively transduction units (TU); IU and TU can be used interchangeably as a quantitative measure of the titer of a viral vector particle preparation. The lentiviral vector is typically non-integrating. The amount of viral particles is at least about $3 \times 10^6$ IU, and can be at least about $1 \times 10^7$ IU, at least about $3 \times 10^7$ IU, at least about $1 \times 10^8$ IU, at least about $3 \times 10^8$ IU, at least about $1 \times 10^9$ IU, or at least about $3 \times 10^9$ IU.

The above-described recombinant vectors may be delivered to host cells according to published methods. The rAAV, preferably suspended in a physiologically compatible carrier, may be administered to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The viral vectors described herein may be used in preparing a medicament for delivering ornithine transcarbamylase to a subject (e.g., a human patient) in need thereof, supplying functional hOTCase to a subject, and/or for treating ornithine transcarbamylase deficiency. A course of treatment may optionally involve repeat administration of the same viral vector (e.g., an AAV8 vector) or a different viral vector (e.g., an AAV8 and an AAVrh10). Still other combinations may be selected using the viral vectors and non-viral delivery systems described herein.

In another embodiment, the nucleic acid sequences described herein may be delivered via a non-viral route. For example, a hOTC sequence may be via a carrier system for expression or delivery in RNA form (e.g., mRNA) using one of a number of carrier systems which are known in the art. Such carrier systems include those provided by commercial entities, such as PhaseRx' so-called "SMARTT" technology. These systems utilize block copolymers for delivery to a target host cell. See, e.g., US 2011/0286957 entitled, "Multiblock Polymers", published Nov. 24, 2011; US 2011/0281354, published Nov. 17, 2011; EP2620161, published Jul. 31, 2013; and WO 2015/017519, published Feb. 5, 2015. See, also, S. Uchida et al, (February 2013) PLoS ONE 8(2): e56220. Still other methods involve generating and injecting synthetic dsRNAs [see Soutschek et al. Nature (2004) 432 (7014): 173-8; see also Morrissey et al. Hepatol. (2005) 41(6): 1349-56], local administration to the liver has also been demonstrated by injecting double stranded RNA directly into the circulatory system surrounding the liver using renal vein catheterization. [See Hamar et al. PNAS (2004) 101(41): 14883-8.]. Still other systems involve delivery of dsRNA and particularly siRNA using cationic complexes or liposomal formulations [see, e.g., Landen et al. Cancer Biol. Ther. (2006) 5(12); see also Khoury et al. Arthritis Rheumatol. (2006) 54(6): 1867-77. Other RNA delivery technologies are also available, e.g., from Veritas Bio [see, e.g., US 2010/0323001, Dec. 23, 2010, "In vivo delivery of double stranded RNA to a target cell" (cytosolic content including RNAs, e.g., mRNA, expressed siRNA/shRNA/miRNA, as well as injected/introduced siRNA/shRNA/miRNA, or possibly even transfected DNA present in the cytosol packaged within exovesicles and be transported to distal sites such as the liver)]. Still other systems for in vivo delivery of RNA sequences have been described. See, e.g., US 2012/0195917 (Aug. 2, 2012) (5'-cap analogs of RNA to improve stability and increase RNA expression), WO 2013/143555A1, Oct. 3, 2013, and/or are commercially available (BioNTech, Germany; Valera (Cambridge, Mass.); Zata Pharmaceuticals).

Thus, in one embodiment, the invention provides an engineered hOTC mRNA of the mature sequence (at least about nt 99-1098) or the full-length of SEQ ID NO: 10, 11, 12, 13, or a sequence having at least 97% to 99% identity thereto, in a composition for delivery of double-stranded or single stranded RNA which results in expression of the mature hOTCase in a target host cell, e.g., a liver cell.

The kinetics of the composition described herein which contain mRNA (delivered directly, as compared to transcribed from a DNA delivery molecule) are particularly well suited for use in subjects in acute crisis, as expression of the hOTCase from the mRNA may be seen within a period of several hours. In order to avoid rapid clearance of the RNA, it is modified as described herein (e.g., using a cap or a modified base), such that its effects may be retained for over 24 hours, over 48 hours, or up to about 3 days (about 72 hours). It may be desirable to co-administer an mRNA directly as described herein and co-administer at the same or substantially the same time, a DNA or viral vector-based hOTC composition as defined herein. Thus, a subject may receive immediate treatment, and at such time as the mRNA-mediated expression begins to wane, the longer-term hOTC expression conferred by a viral vector-mediated expression begins to take effect. Alternatively, a subject may receive a second administration of an mRNA-based composition as defined herein. The mRNA compositions described herein may be used in other therapeutic regimens or methods, including those involving OTCD patients who are not in acute crisis.

The compositions according to the present invention may comprise a pharmaceutically acceptable carrier, such as defined above. In one embodiment, the composition comprises a block copolymer associated with a hOTC polynucleotide as described herein. The block copolymers may form a micelle, such that the micelle comprises a plurality of block copolymer.

Typically, such a composition contains a nucleic acid molecule comprising the mRNA sequence corresponding to the hOTC sequence encoding the mature hOTCase (at least about nt 99 to 1098) or the full-length of any of SEQ ID NO: 10, 11, 12, 13. In addition, this nucleic acid molecule may include the 5' untranslated region (UTR), also known as the leader sequence or leader RNA, and one or more of an optional intron(s), an optional exon(s), an optional a Kozak sequence, an optional WPRE. and a polyA, and the 3' UTR flanking the coding sequences. Suitable leader sequences include those discussed above in connection with the hOTC DNA sequences, which discussion is incorporated by reference herein. Examples of sources of suitable leader sequences, other than the native hOTC leader sequences, or those corresponding to FIG. 2, FIG. 3 or FIG. 4, or FIG. 5 are discussed above. Similarly, sources of suitable introns, polyA, and Kozak sequences are discussed above and are applicable to the delivery of the corresponding RNA sequences discussed in the present paragraph. Further, various modifications to the RNA may be generated, e.g., a modified 5' cap structure may be engineered into the construct in order to avoid rapid clearance of the mRNA in vivo, or for another desired reason. Methods of generating such 5' cap structures is known to those of skill in the art. See, e.g., US 2012/0195917 and WO 2013/143555A1, Oct. 3, 2013. In addition, modified nucleotides can be used to make mRNA in vitro, like pseudouridine. Also RNA may be dosed repetitively, or subject can be dosed first with mRNA to manage neonatal crises followed up by viral vector-mediated delivery (e.g., AAV) for long term therapy and to prevent fibrosis/cirrhosis and/or hepatocellular carcinoma.

mRNA can be synthesized from the hOTC DNA sequences described herein, using techniques that are well known in the art. For example, Cazenave C, Uhlenbeck O C, RNA template-directed RNA synthesis by T7 RNA polymerase. Proc Natl Acad Sci USA. 1994 Jul. 19; 91(15): 6972-6, describe the use of the T7 RNA polymerase for generating RNA from cDNA or RNA templates. See also, Wichlacz Al, Legiewicz M, Ciesiolka J., Generating in vitro transcripts with homogenous 3 ends using trans-acting antigenomic delta ribozyme, Nucleic Acids Res. 2004 Feb. 18; 32(3):e39; Krieg P A, Melton D A., Functional messenger RNAs are produced by SP6 in vitro transcription of cloned cDNAs, Nucleic Acids Res. 1984 Sep. 25; 12(18):7057-70; and Rio, D. C., et al. RNA: A Laboratory Manual. Cold Spring Harbor: Cold Spring Harbor Laboratory Press, 2011, 205-220. Each of these references is incorporated herein by reference. In addition, kits and protocols for generating mRNA are available commercially including, without limitation, the Riboprobe® In Vitro Transcription System (Promega Corp.); RiboMAX™ Large Scale RNA Production Systems (Promega Corp.); MAXIscript Kit (Ambion); MEGIscript Kit (Ambion); MessageAmp™ aRNA Kit (Ambion); mMESSAGE mMACHINE® Kits (Ambion); and HiScribe™ T7 High Yield RNA Synthesis Kit (New England Biolabs® Inc.). Custom RNA can also be generated commercially from companies including, without limitation, TriLink Biotechnologies; bioSYNTHESIS; GE Dharmacon; and IBA Lifesciences.

The hOTC DNA sequences described herein can be generated in vitro and synthetically, using techniques well known in the art. For example, the PCR-based accurate synthesis (PAS) of long DNA sequence method may be utilized, as described by Xiong et al, PCR-based accurate synthesis of long DNA sequences, Nature Protocols 1, 791-797 (2006). A method combining the dual asymmetrical PCR and overlap extension PCR methods is described by Young and Dong, Two-step total gene synthesis method, Nucleic Acids Res. 2004; 32(7): e59. See also, Gordeeva et al, J Microbiol Methods. Improved PCR-based gene synthesis method and its application to the *Citrobacter freundii* phytase gene codon modification. 2010 May; 81(2):147-52. Epub 2010 Mar. 10; see, also, the following patents on oligonucleotide synthesis and gene synthesis, Gene Seq. 2012 April; 6(1):10-21; U.S. Pat. No. 8,008,005; and U.S. Pat. No. 7,985,565. Each of these documents is incorporated herein by reference. In addition, kits and protocols for generating DNA via PCR are available commercially. These include the use of polymerases including, without limitation, Taq polymerase; OneTaq® (New England Biolabs); Q5® High-Fidelity DNA Polymerase (New England Biolabs); and GoTaq® G2 Polymerase (Promega). DNA may also be generated from cells transfected with plasmids containing the hOTC sequences described herein. Kits and protocols are known and commercially available and include, without limitation, QIAGEN plasmid kits; Chargeswitch® Pro Filter Plasmid Kits (Invitrogen); and GenElute™ Plasmid Kits (Sigma Aldrich). Other techniques useful herein include sequence-specific isothermal amplification methods, that eliminate the need for thermocycling. Instead of heat, these methods typically employ a strand-displacing DNA polymerase, like Bst DNA Polymerase, Large Fragment (New England Biolabs), to separate duplex DNA. DNA may also be generated from RNA molecules through amplification via the use of Reverse Transcriptases (RT), which are RNA-dependent DNA Polymerases. RTs polymerize a strand of DNA that is complimentary to the original RNA template and is referred to as cDNA. This cDNA can then be further amplified through PCR or isothermal methods as outlined above. Custom DNA can also be generated commercially from companies including, without limitation, GenScript; GENEWIZ®; GeneArt® (Life Technologies); and Integrated DNA Technologies.

The term "expression" is used herein in its broadest meaning and comprises the production of RNA or of RNA and protein. With respect to RNA, the term "expression" or "translation" relates in particular to the production of peptides or proteins. Expression may be transient or may be stable.

The term "translation" in the context of the present invention relates to a process at the ribosome, wherein an mRNA strand controls the assembly of an amino acid sequence to generate a protein or a peptide.

According to the present invention, a "therapeutically effective amount" of the hOTC is delivered as described herein to achieve a desired result, i.e., treatment of OTC deficiency or one or more symptoms thereof. As described herein, a desired result includes reducing orotic acid levels, reducing hyperammonemia and/or minimizing or eliminating one or more of the neurophysical complications including developmental delay, learning disabilities, intellectual disability, attention deficit hyperactivity disorder, and executive function deficits. Treatment may include treatment of subjects having severe neonatal-onset disease (males or, more rarely, females), and late-onset (partial) disease in males and females, which may present from infancy to later childhood, adolescence, or adulthood. In certain embodiments, the invention provides a method of treating and/or preventing fibrosis and/or cirrhosis in subjects, particularly those late-onset heterozygous subjects by administering hOTC as described herein. In one embodiment, therapeutic goals for OTC deficiency are to maintain plasma ammonia at less than <80 μmol/L, plasma glutamine <1,000 μmol/L, argininemia 80-150 μmol/L and branched chain amino acids within the normal range. However, other therapeutic endpoints may be selected by the treating physician.

In yet another embodiment, the invention provides a method of rescuing and/or treating a neonatal subject OTCD comprising the step of delivering a hOTC gene to the liver of a newborn subject (e.g., a human patient). This method may utilize any nucleic acid sequence encoding a functional hOTCase, whether a synthetic hOTC as described herein or a wild-type hOTC, or a hOTC from another source, or a combination thereof. In one embodiment, neonatal treatment is defined as being administered a hOTC as described herein within 8 hours, the first 12 hours, the first 24 hours, or the first 48 hours of delivery. In another embodiment, particularly for a primate, neonatal delivery is within the period of about 12 hours to about 1 week, 2 weeks, 3 weeks, or about 1 month, or after about 24 hours to about 48 hours. To address dilution due to the rapid turnover of liver cells in a growing mammal (e.g., a non-human or human primate), neonatal therapy is desirably followed by readministration at about 3 months of age, about 6 months, about 9 months, or about 12 months. Optionally, more than one readministration is permitted. Such readministration may be with the same type of vector, a different viral vector, or via non-viral delivery. In one embodiment, an RNA based delivery system for functional hOTC is used to stabilize a subject (e.g., a human patient) in crisis, followed by delivery of a viral vector mediated delivery of a functional hOTC. In another embodiment, initial therapy involves co-administration of viral and non-viral-mediated hOTC delivery systems. In a further embodiment, the hOTC DNA and RNA constructs may be used alone, or in combination with the standard of care for the patient's diagnosis and condition.

As described in the working examples herein, the inventors have found that heterozygous OTCD subjects, including those with late onset OTCD, have increased fibrosis and/or microvesicular steatosis throughout the liver. Such liver fibrosis and/or microvesicular steatosis can lead to OTCD-related cirrhosis. Thus, in another embodiment, the invention provides methods of preventing liver fibrosis and/or the associated medical condition OTCD-related cirrhosis by delivering to the subject (e.g., a human patient) a hOTC. This aspect of the invention may utilize a viral or non-viral delivery system. The nucleic acid expression cassette may contain a synthetic hOTC DNA or RNA as provided herein, or another suitable sequence which expresses functional hOTCase. In one embodiment, a method of treating and/or preventing liver fibrosis, microvesicular steatosis, and/or OTCD-related cirrhosis is provided which involves delivering OTCase to a subject having OTCD. The subject may be a human patient. In one embodiment, the patient is heterozygous and has late onset OTCD. The patient may have been previously untreated for OTCD, or may have received other conventional treatments. At present, there is no existing standard of care for OTCD, but rather symptoms are managed, e.g., through discontinuation of protein intake, compensatory increases in dietary carbohydrates and lipids, hemodialysis for comatose patients with extremely high blood levels; and/or intravenous administration of sodium benzoate, arginine, and/or sodium phenylacetate. The US FDA has approved glycerol phenylbutyrate (Ravicti®) for long-term management of some urea cycle disorders for patients aged 2 years and older; this drug helps rid the body of ammonia and is intended for patients who cannot be managed by a protein-restricted diet or amino acid supplements alone. In one embodiment, treatment of the patient (e.g., a first injection) is initiated prior to the first year of life. In another embodiment, treatment is initiated after the first 1 year, or after the first 2 to 3 years of age, after 5 years of age, after 11 years of age, or at an older age.

In one embodiment, the method of the invention provides for treating and/or reversing liver fibrosis and/or OTCD-related cirrhosis by delivering to the subject a functional OTCase which is encoded by an engineered DNA of SEQ ID NO: 1, 3, 4, 5, 8 or 9, or a chimeric DNA as defined herein. Delivery of the DNA may be mediated by a viral vector containing the engineered DNA in an expression cassette, or by a non-viral delivery system, either of which mediates expression of functional OTCase in the liver cells of the subject. In another embodiment, the subject is administered an engineered RNA of SEQ ID NO: 10, 11, 12 or 13, or a chimeric RNA as defined herein. Delivery of the RNA may be mediated by a viral vector containing the engineered RNA in an expression cassette, or by a non-viral delivery system, either of which mediates expression of functional OTCase in the liver cells of the subject.

Heterozygous OTCD subjects have an increased risk of developing hepatocellular carcinoma (HCC). See, e.g., J M Wilson et al, Molecular Genetics and Metabolism (2012), Mol Genet Metab. 2012 February; 105(2): 263-265, Published online 2011 Nov. 7. Thus, in another embodiment, the invention provides methods of preventing treating and/or preventing HCC by delivering to the subject (e.g., a human patient) a hOTC. This aspect of the invention may utilize a viral or non-viral delivery system. The nucleic acid expression cassette may contain a synthetic hOTC DNA or RNA as provided herein, or another suitable sequence which expresses functional hOTCase. The patient may have been previously untreated for OTCD, or may have received other conventional treatments, i.e., standard of care. In one embodiment, treatment of the patient (e.g., a first injection) is initiated prior diagnosis with HCC. In another embodiment, treatment of the patient is initiated following HCC diagnosis. Optionally, treatment involves co-administration with sorafenib (commercially available as Nexavar®), or being used in conjunction with chemoembolization, radiation, thermal ablation, percutaneous ethanol injection, targeted therapy (e.g., anti-angiogenesis drugs), hepatic arterial infusion of anti-cancer drugs, immunotherapy, or with surgical options including, e.g., resection, cryosurgery, and liver transplant. When used for treatment of HCC, it may be desirable to select a non-integrating delivery system (e.g., direct RNA delivery, or non-integrating viruses such as adenoviruses or non-integrating lentiviruses) for delivery of a synthetic hOTC DNA or RNA as described herein.

By "functional OTC", is meant a gene which encodes the wild-type OTCase such as characterized by SEQ ID NO: 2 or another OTCase which provides at least about 50%, at least about 75%, at least about 80%, at least about 90%, or about the same, or greater than 100% of the biological activity level of the wild-type human ornithine transcarbamylase enzyme, which may be characterized by the sequence of SEQ ID NO:2 or a natural variant or polymorph thereof which is not associated with disease. More particularly, as heterozygous patients may have as low an OTCase functional level as about 50% or lower, effective treatment may not require replacement of OTCase activity to levels within the range of "normal" or non-OTCD patients. Similarly, patients having no detectable amounts of OTCase may be rescued by delivering OTCase function to less than 100% activity levels, and may optionally be subject to further treatment subsequently. As described herein, the gene therapy described herein, whether viral or non-viral, may be used in conjunction with other treatments, i.e., the standard of care for the subject's (patient's) diagnosis.

In one embodiment, such a functional OTCase has a sequence which has about 95% or greater identity to the mature protein (i.e., about the last 322 amino acids) or full-length sequence of SEQ ID NO: 2, or about 97% identity or greater, or about 99% or greater to SEQ ID NO: 2 at the amino acid level. Such a functional OTCase may also encompass natural polymorphs which are not associated with any disease (e.g., F101, L111, and/or WI193-194 of SEQ ID NO:2). Identity may be determined by preparing an alignment of the sequences and through the use of a variety of algorithms and/or computer programs known in the art or commercially available [e.g., BLAST, ExPASy; ClustalO; FASTA; using, e.g., Needleman-Wunsch algorithm, Smith-Waterman algorithm].

A variety of assays exist for measuring OTC expression and activity levels in vitro. See, e.g., X Ye, et al, 1996 Prolonged metabolic correction in adult ornithine transcarbamylase-deficient mice with adenoviral vectors. J Biol Chem 271:3639-3646) or in vivo. For example, OTC enzyme activity can be measured using a liquid chromatography mass spectrometry stable isotope dilution method to detect the formation of citrulline normalized to [1,2,3,4,5-13C5] citrulline (98% 13C). The method is adapted from a previously developed assay for detection of N-acetylglutamate synthase activity [Morizono H, et al, Mammalian N-acetylglutamate synthase. Mol Genet Metab. 2004; 81(Suppl 1):S4-11.]. Slivers of fresh frozen liver are weighed and briefly homogenized in buffer containing 10 mM HEPES, 0.5% Triton X-100, 2.0 mM EDTA and 0.5 mM DTT. Volume of homogenization buffer is adjusted to obtain 50 mg/ml tissue. Enzyme activity is measured using 250 µg liver tissue in 50 mM Tris-acetate, 4 mM ornithine, 5 mM carbamyl phosphate, pH 8.3. Enzyme activity is initiated with the addition of freshly prepared 50 mM carbamyl phosphate dissolved in 50 mM Tris-acetate pH 8.3, allowed to proceed for 5 minutes at 25° C. and quenched by addition of an equal volume of 5 mM13C5-citrulline in 30% TCA. Debris is separated by 5 minutes of microcentrifugation, and the supernatants are transferred to vials for mass spectroscopy. Ten µL of sample are injected into an Agilent 1100 series LC-MS under isocratic conditions with a mobile phase of 93% solvent A (1 ml trifluoroacetic acid in 1 L water):7% solvent B (1 ml trifluoroacetic acid in 1 L of 1:9 water/acetonitrile). Peaks corresponding to citrulline [176.1 mass:charge ratio (m/z)] and 13C5-citrulline (181.1 m/z) are quantitated, and their ratios are compared to ratios obtained for a standard curve of citrulline run with each assay. Samples are normalized to either total liver tissue or to protein concentration determined using a Bio-Rad protein assay kit (Bio-Rad, Hercules, Calif.). Other assays, which do not require liver biopsy, may also be used. One such assay is a plasma amino acid assays in which the ratio of glutamine and citrulline is assessed and if glutamine is high (>800 microliters/liter) and citrulline is low (e.g., single digits), a urea cycle defect is suspected. Plasma ammonia levels can be measured and a concentration of about 100 micromoles per liter is indicative of OTCD. Blood gases can be assessed if a patient is hyperventilating; respiratory alkalosis is frequent in OTCD. Orotic acid in urine, e.g., greater than about 20 micromoles per millimole creatine is indicative of OTCD, as is elevated urinary orotate after allopurinol challenge test. Diagnostic criteria for OTCD have been set forth in Tuchman et al, 2008, Urea Cycle Disorders Consortium (UCDC) of the Rare Disease Clinical Research Network (RDCRN). Tuchman M, et al., Consortium of the Rare Diseases Clinical Research Network. Cross-sectional multicenter study of patients with urea cycle disorders in the United States. Mol Genet Metab. 2008; 94:397-402, which is incorporated by reference herein. See, also, www.ncbi.nlm.nih.gov/books/NBK154378/, which provides a discussion of the present standard of care for OTCD.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% (±10%) from the reference given, unless otherwise specified.

The term "regulation" or variations thereof as used herein refers to the ability of a compound of formula (I) to inhibit one or more components of a biological pathway.

A "subject" is a mammal, e.g., a human, mouse, rat, guinea pig, dog, cat, horse, cow, pig, or non-human primate, such as a monkey, chimpanzee, baboon or gorilla.

As used herein, "disease", "disorder" and "condition" are used interchangeably, to indicate an abnormal state in a subject.

Unless defined otherwise in this specification, technical and scientific terms used herein have the same meaning as commonly understood by one of ordinary skill in the art and by reference to published texts, which provide one skilled in the art with a general guide to many of the terms used in the present application.

The following examples are illustrative only and are not intended to limit the present invention.

Example 1—scAAV Vectors Containing hOTC pAAVsc.TBG.hOTCwt and pAAVsc.TBG.hOTCco-LW4 were constructed by replacing the mOTC coding sequencing with wild-type (WT) hOTC (hOTCwt) or hOTCcoLW cDNA, respectively, in a plasmid derived from the previously described pAAVsc.TBG.mOTC1.3 with the intron disrupted [Moscioni D, et al, "Long-term correction of ammonia metabolism and prolonged survival in ornithine transcarbamylase-deficient mice following liver-directed treatment with adeno-associated viral vectors", Mol Ther. 2006; 14:25-33; Cunningham S C, et al, "AAV2/8-mediated correction of OTC deficiency is robust in adult but not neonatal Spf(ash) mice", Mol Ther. 2009; 17:1340-1346; Wang L, et al., "Sustained correction of OTC deficiency in $spf^{ash}$ mice using optimized self-complementary AAV2/8 vectors", Gene Ther. 2012 April; 19(4):404-10, Epub 2011 Aug. 18].

The scAAV2/8.TBG.hOTCco-LW4 contains an AAV2 3' ITR and a 5' ITR with a deletion in the D-sequence and trs (terminal resolution site), a TBG promoter, the hOTCco-LW4 gene, and a 137 bp 5V40 polyA. The two vector preps (AAV2/8sc.TBG.hOTCwt and AAV2/8sc.TBG.hOTCco-LW4) used in the initial comparison study were purified by two rounds of cesium chloride gradient centrifugation, as previously described [Wang L, et al, Systematic evaluation of AAV vectors for liver directed gene transfer in murine models. Mol Ther. 2010; 18:118-125]. Vectors used in the rest of the study were produced by a scaled production method based on polyethylenimine (PEI) transfection and purified from supernatant or total lysate by iodixanol gradient centrifugation as described [Lock M, et al, Hum Gene Ther. 2010; 21:1259-1271]. Genome titers [genome copies (GC)/ml] of AAV vectors were determined by real-time PCR using primer and probe sets targeting the TBG promoter (forward primer 5'-AAACTGCCAATTCCACTGCTG-3' [SEQ ID NO: 14], reverse primer 5'-CCATAG-GCAAAAGCACCAAGA-3' [SEQ ID NO:15], probe 6FAM-TTGGCCCAATAGTGAGAACTTTTTCCTGC [SEQ ID NO: 16]—TAMRA), and using a linearized plasmid as the standard. The forward primer is located 400 bp downstream of the 5' closed hairpin. Fagone et al [Systemic errors in quantitative polymerase chain reaction titration of self-complementary adeno-associated viral vectors and improved over alternative methods, Hum Gene Ther Methods. 2012 February; 23(1):1-7.] recently reported that the quantitative PCR (Q-PCR) method could significantly underestimate the titer of scAAV vectors, especially when the PCR primers were close to the closed hairpin of the scAAV vector. The titer of one lot of AAV2/8sc.TBG.hOTCco-LW4 vector using a primer and probe set targeting the polyA region (1900 bp downstream of the 5' closed hairpin), and the genome titer was 1.1-fold of the original titer, which was within the intra-assay error of Q-PCR.

OTC protein expression levels and OTC activity were evaluated in the liver of $spf^{ash}$ mice 14 days after i.v. injection of $1 \times 10^{11}$ GC of AAV2/8sc.TBG.hOTCwt or AAV2/8sc.TBG.hOTCco-LW4 vectors. The $spf^{ash}$ mice are a model for late onset OTC disease in humans. All animal procedures were performed in accordance with protocols approved by the Institutional Animal Care and Use Committee (IACUC) of the University of Pennsylvania. $Spf^{ash}$ mice were maintained at the Animal Facility of the Translational Research Laboratories at the University of Pennsylvania as described previously. Three to six months old $spf^{ash}$ mice and their normal littermates were used in the studies. Vectors were administered by intravenous (i.v.) injection via the tail vein. The extent of gene transfer based on resident vector genomes was not statistically different between the two groups. Urine samples were collected before and at various time points after vector treatment for orotic acid analysis as previously described [Moscioni D, et al, Long-term correction of ammonia metabolism and prolonged survival in ornithine transcarbamylase-deficient mice following liver-directed treatment with adeno-associated viral vectors. Mol Ther. 2006; 14:25-33].

Western blot analysis to detect hOTC expression in liver lysate was performed as previously described [Wang L, et al, 2012, epub 2011)]. The primary antibody to detect hOTC was a custom rabbit polyclonal antibody provided by Hiroki Morizono's laboratory at the Children's National Medical Center. Liver lysates (10 μg/lane) were also blotted and probed by an anti-tubulin antibody (Abcam, Cambridge, Mass.). Western analysis demonstrated 100-fold higher expression of hOTC from the hOTCco-LW4 vector as compared to the hOTCwt vector, reaching levels in slight excess of those seen in WT mice.

OTC enzyme activity was measured using a liquid chromatography mass spectrometry stable isotope dilution method to detect the formation of citrulline normalized to [1,2,3,4,5-13C5] citrulline (98% 13C). The method is adapted from a previously developed assay for detection of N-acetylglutamate synthase activity [Morizono H, et al, Mammalian N-acetylglutamate synthase. Mol Genet Metab. 2004; 81(Suppl 1):S4-11.]. Slivers of fresh frozen liver were weighed and briefly homogenized in buffer containing 10 mM HEPES, 0.5% Triton X-100, 2.0 mM EDTA and 0.5 mM DTT. Volume of homogenization buffer was adjusted to obtain 50 mg/ml tissue. Enzyme activity was measured using 250 μg liver tissue in 50 mM Tris-acetate, 4 mM ornithine, 5 mM carbamyl phosphate, pH 8.3. Enzyme activity was initiated with the addition of freshly prepared 50 mM carbamyl phosphate dissolved in 50 mM Tris-acetate pH 8.3, allowed to proceed for 5 minutes at 25° C. and quenched by addition of an equal volume of 5 mM13C5-citrulline in 30% TCA. Debris was separated by 5 minutes of microcentrifugation, and the supernatants were transferred to vials for mass spectroscopy. Ten μL of sample was injected into an Agilent 1100 series LC-MS under isocratic conditions with a mobile phase of 93% solvent A (1 ml trifluoroacetic acid in 1 L water):7% solvent B (1 ml trifluoroacetic acid in 1 L of 1:9 water/acetonitrile). Peaks corresponding to citrulline [176.1 mass:charge ratio (m/z)]

and 13C5-citrulline (181.1 m/z) were quantitated, and their ratios were compared to ratios obtained for a standard curve of citrulline run with each assay. Samples were normalized to either total liver tissue or to protein concentration determined using a Bio-Rad protein assay kit (Bio-Rad, Hercules, Calif.).

The vector carrying engineered hOTC cDNA termed herein LW4 (FIG. 4) was found to improve expressed hOTC protein levels by 100-fold. An assessment of OTC enzyme activity generally correlated with the OTC Western blot experiments although OTC protein was more elevated than OTC enzyme activity when compared to endogenous OTC. When subtracting the background activity levels in the spfash mice, the hOTCco-LW4 resulted in over 33-fold higher activity than the hOTCwt. Sustained and dose-correlated hOTC expression and activity levels were observed in the treated spf$^{ash}$ mice. Compared to a previously described murine OTC vector which differed mainly in the cDNA, the vector carrying the hOTCco-LW4 vector was about 10-fold more potent.

The illustrative vector carrying the modified hOTCco-LW4 (FIG. 4) provided high level of transduction, as measured by OTC histological assays, throughout a broad range of doses. Between doses $1\times10^{11}$ GC and $3\times10^9$ GC, transduction efficiency, as measured by histochemical staining, varied between 50-70%. At the lowest dose of $1\times10^9$ GC, 40% of the liver areas were positive by OTC histochemical staining. The lack of a clear dose effect by histochemistry and immunostaining could be due to the fact that codon optimization significantly improved hOTC expression in the transduced hepatocytes. This leads to improved sensitivity to detect transduced cells with low vector genome copies. Transduction could be saturated with high vector doses ($1\times10^{11}$-$1\times10^{10}$ GC), and therefore transduction efficiency measured by in situ detection methods would not discriminate between low and high dose groups in contrast to OTC enzyme activity on liver lysates measured by mass spectrometry.

A further study was performed in which neonatal expression of hOTC was assessed in spf$^{ash}$ mice, injected on day 1 of life, using the scAAV2/8.TBG.hOTCco at a dose of $5\times10^{10}$ GC/pup injected via the temporal vein. Robust expression was detected at 24 and 48 hours. Additional studies were performed using doses of $1\times10^{11}$, $3\times10^{10}$, and $1\times10^{10}$, and assessed for 12 weeks. Over the 16 week period of the study, a reduction in the initial robust expression levels was observed at each of the doses. This is believed to be due to dilution, i.e., a natural result of the proliferation of liver cells in growing animals. Thus, while initial restoration of OTC liver activity is observed following neonatal gene transfer in spf$^{ash}$ mice, this result is temporary, with OTC activity dropping from about 1000% of wild-type (wt) levels at about 1 week, to about 50% of wt levels at 4 weeks, to about 10% of wt levels at 12 weeks ($1\times10^{11}$ GC level); or about 500% of wt levels at week 1, to about 20% of wt levels, or about 10% of wt levels at week 1 ($3\times10^{10}$ GC dose) or about 200% wt levels at week 1, to about 10% wt levels at week 4 ($1\times10^{10}$ GC dose). In one study, using animals receiving the first injection of $3\times10^{10}$ GC at day 1, animals were injected with a second AAV vector carrying the hOTCco gene (scAAVrh10.hOTCco; $1.8\times10^{10}$ GC) at week 4. As a control, one group of animals received no readministration and one group received only the second vector at 4 weeks. Readministration of the AAV.hOTCco resulted in restoration of liver OTC activity.

Further studies were designed to assess the ability to rescue OTC-KO pups by neonatal gene therapy, both short-term and long-term.

Example 2—Production of scAAV Vectors Having Codon Optimized Sequences

A. scAAV8.TBG.hOTC-co

Plasmids containing a codon optimized hOTC sequence of SEQ ID NO: 3, 4, 5, 9 or 10, respectively, are cloned as described in Example 1 by replacing the mOTC coding sequencing with hOTCco in a plasmid derived from the previously described pAAVsc.TBG.mOTC1.3 with the intron. The resulting plasmid pAAVsc.TBG.hOTCco is cloned into an AAV8 capsid [Gao et al, PNAS USA, 2002, 99:11854-11859] using conventional techniques.

B. scAAVrh10.TBG.hOTC-co

Plasmids containing a codon optimized hOTC sequence of SEQ ID NO: 3, 4, 5, 9 or 10, respectively, are cloned as described in Example 1 by replacing the mOTC coding sequencing with hOTCco in a plasmid derived from the previously described pAAVsc.TBG.mOTC1.3 with the intron. The resulting plasmids pAAVsc.TBG.hOTCco are cloned into a AAVrh10 capsid [Gao et al, PNAS USA, 2002, 99:11854-11859] using conventional techniques.

Example 3—Production of ssAAV Vectors Having Codon Optimized Sequences ssAAV2/8.LSP1.hOTC-co Plasmids containing the codon optimized hOTCco sequences are cloned as described by replacing the mOTC coding sequencing of the pLSP1mOTC plasmid [Cunningham et al, Mol Ther, 2009, 17: 1340-1346] with the corresponding cDNA sequence of SEQ ID NO:3, 4, 5, 9 or 10. The resulting plasmids pAAVsc.LSPLhOTCco are cloned into AAV8 capsids to form the corresponding ssAAV2/8.LSP1.hOTC-co vectors using techniques described in Example 1.

B. ssAAV2/rh10.LSP1.hOTC-co

Plasmids containing the codon optimized hOTCco sequences are cloned as described by replacing the mOTC coding sequencing of the pLSP1mOTC plasmid [Cunningham et al, Mol Ther, 2009, 17: 1340-1346] with the corresponding cDNA sequence of SEQ ID NO:3, 4, 5, 9 or 10. The resulting plasmids pAAVsc.LSPLhOTCco are cloned into AAV8 capsids to form the corresponding ssAAV2/8.LSP1.hOTC-co vectors using techniques described in Example 1.

The vectors generated according to Part A or B may be purified by two rounds of cesium chloride gradient centrifugation, buffered-exchanged with PBS, and concentrated using Amicon Ultra 15 centrifugal filter devices-100K (Millipore, Bedford, Mass.). Genome titer (GC/me of AAV vectors can be determined by real-time PCR using a primer/probe set corresponding to the TBG promoter and linearized plasmid standards. Vectors can be subject to additional quality control tests including sodium dodecyl sulfate-polyacrylamide gel electrophoresis (SDS-PAGE) analysis for vector purity and Limulus amebocyte lysate (LAL) for endotoxin detection (Cambrex Bio Science, Walkersville, Md., USA).

Example 4—ssAAV8.TBG.hOTCco in Model of Late Onset of OTCD

An AAV8 vector was generated using the methods described herein. The vector has packaged therein a 5' AAV2

ITR, a TBG promoter, an intron, a hOTCco, a WPRE element, a bovine growth hormone polyA, and a 3' AAV2 ITR. The expression and kinetics of this vector was compared to a self-complementary AAV8 vector with or without the WPRE element. The results show that the single-stranded constructs with the WPRE element outperformed those vectors lacking the WPRE element; at comparable doses both single-stranded vectors (with and without WPRE) were less robust than the self-complementary vector lacking WPRE in the time points measured.

However, the single-stranded vectors may have other desirable properties, e.g., in terms of kinetics, depending upon the age and condition of the patient.

Example 5—Production of Adenovirus Vectors Having Codon Optimized Sequences hOTCco cDNA [SEQ ID NO: 3, 4, 5, 9 and 10] with NotI linkers is cloned downstream of a rat PEPCK promoter to generate pPEPCK-hOTC as described in A. Mian et al, Molecular Therapy, 2004, 10: 492-499 (2004). This plasmid is digested with AscI, and the resultant PEPCK-hOTCco fragment is inserted into the adenoviral backbone plasmid pC4HSU31 to generate the parental plasmids pC4HSU-PEPCK-hOTCco. Plasmid pWPRE is digested with ClaI to release the WPRE, which is then inserted into the MluI site of pPEPCK-hOTC, to generate pPEPCK-hOTCco-WPRE plasmid with their respective hOTCco sequences. The remaining steps to generate the adenoviral plasmid pC4HSU-PEPCK-hOTCco-WPRE are as previously described. All cloning sites are confirmed by DNA sequence analysis. The identity of recombinant adenoviral plasmids can be confirmed by restriction enzyme digestion with HindIII and BamHI. The adenoviral plasmids are linearized with PmeI before transfection into 293Cre4 cells. Adenoviral vectors are rescued and amplified with 293Cre4 cells and helper virus AdLC8cluc. Suspension 293N3Scre8 cells may be used in the final step of vector production. Purification, quantification by OD260 and viral DNA extraction are performed as described in detail elsewhere [Brunetti-Pieni, N., et al. (2004). Acute toxicity after high-dose systemic injection of helper-dependent adenoviral vectors into non-human primates. Hum. Gene Ther. 15: 35-46; Ng, P., Parks, R. J. and Graham, F. L. (2002). Preparation of helper-dependent adenoviral vectors. *Methods Mol. Med.* 69: 371-388].

Example 6—Production of hOTCco Lentiviral Vectors

A. Replication-defective lentiviral vectors containing the hOTCco sequences provided herein can be produced by replacing the rat OTC gene sequence insert of the plasmid pLenti-GIII-CMV-GFP-2A-Puro [commercially available from Applied Biological Materials (ABM) Inc.; Canada] with the desired hOTCco sequence [SEQ ID NO: 3, 4, 5, 9 and 10]. The viruses are generated according to manufacturer instructions. The ABM system includes an enhancer deletion in the U3 region of 3'ΔLTR to ensure self-inactivation of the lentiviral vector following transduction and integration into the target cell's genomic DNA; contains minimal lentiviral genes necessary for packaging, replication and transduction (Gag/Pol/Rev), derived from different plasmids all lacking packaging signals; further, none of the Gag, Pol, or Rev genes are incorporated into in the packaged viral genome, thus making the mature virus replication-incompetent.

B. Replication-Defective, Non-Integrating hOTC Lentiviral Vectors

A DNA construct containing a liver specific promoter and the hOTCco DNA of SEQ ID NO: 3, 4, 5, 9 and 10 are engineered into lentivirus vectors which are pseudotyped into sindbis virus E2 enveloped produced as described in US2011/0064763, which is incorporated by reference herein, All vectors contain splice donor, packaging signal (psi), a Rev-responsive element (RRE), splice donor, splice acceptor, central poly-purine tract (cPPT). The WPRE element is eliminated in certain viruses.

C. The hOTCco DNA of SEQ ID NO: 3, 4, 5 9 and 10, is cloned into a lentivirus pseudotyped with a vesicular stomatitis virus (VSV) envelope gene, purchased from InvivoGen (SanDiego, Calif.) using manufacturer's instructions.

Example 7—Production hOTCco RNA Delivery Systems

RNA may be prepared by in vitro transcription from a DNA template or synthesized. The RNA expression cassette is prepared which includes a 5' UTR, an optional intron with splice donor and acceptor sites, an optional Kozak sequence, the hOTC coding sequence provided herein, a polyA, and a 3' UTR using known techniques.

A. A suitable amount of mRNA are incorporated into a lipid-enveloped pH-responsive polymer nanoparticles generated using published techniques. [X. Su et al, Mol. Pharmaceutics, 2011, 8 (3), pp 774-787; web publication: Mar. 21, 2011].

B. Polymeric nanoparticle formulations with 25 kDa branched polyethyleneimine (PEI) are prepared as follows. When PEI is present, it may be branched PEI of a molecular weight ranging from 10 to 40 kDa, e.g., 25 kDa branched PEI (Sigma #408727). Additional exemplary polymers suitable for the present invention include those described in PCT Publication WO2013182683, the contents of which is hereby incorporated by reference. The required amount of mRNA is diluted just before application in water for injection (Braun, Melsungen) to a total volume of 4 ml and added quickly to 4 ml of an aqueous solution of branched PEI 25 kDa using a pipette at an N/P ratio of 10. The solution is mixed by pipetting up and down.

C. For a lipid-based nanoparticle, a lipid formulation is created using expression cassette containing the hOTCco RNA in a formulation of cK-E12:DOPE:Chol:PEG-DMG2K (relative amounts 50:25:20:5 (mg:mg:mg:mg)) to provide a solution for delivery. The cationic lipid cK-E12 is used (see, e.g., WO 2013/063468), and is combined with dioleoylphosphatidyl-ethanolamine or "DOPE", cholesterol (chol), and polyethylene glycol (PEG) or a PEGylated lipid (PEG-DMG2K) using e formulation methods described in international patent publications WO 2010/053572 and WO 2012/170930, both of which are incorporated herein by reference.

Example 8—hOTCco DNA Delivery Systems

A. Naked Plasmid DNA—The hOTCco sequences [SEQ ID NO: 3, 4, or 5] are engineered as naked plasmid DNA constructs which are delivered to a target liver cell (e.g., via intravascular administration) and express the human OTC protein in the target cell.

B. Cationic lipid-DNA complexes—Cationic lipid-DNA complexes are prepared using a suitable amount of an expression cassette containing at least a promoter, an optional intron, an optional Kozak sequences, an hOTCco of SEQ ID NO: 3, 4 or 5, a polyA, and other optional expression control sequences. The promoter may be a liver specific promoter. Alternatively, another non-tissue specific promoter may be selected. For example, a suitable amount of DNA is formulated with a cationic lipid of cK-E12: DOPE:Chol:PEG-DMG2K (relative amounts 50:25:20:5 (mg:mg:mg:mg)) to form a cationic lipid-DNA complex suitable for delivery to a subject. The cationic lipid cK-E12 is used (see, e.g., WO 2013/063468), and is combined with dioleoylphosphatidyl-ethanolamine or "DOPE", cholesterol (chol), and polyethylene glycol (PEG) or a PEGylated lipid (PEG-DMG2K) using e formulation methods described in international patent publications WO 2010/053572 and WO 2012/170930, both of which are incorporated herein by reference.

Example 9—Long-Term Correction of a Neonatal Lethal Form of OTC Deficiency by Multiple Treatments with AAV Vectors of Different Serotypes In the current study, the scAAV8.TBG.hOTCcoLW4 prepared as described in Example 1 was used to rescue animals in a mouse model of neonatal (early) onset OTCD. OTC KO mice were generated through the deletion of exons 2-3, and the properties of this mouse characterized in terms of similarity to human patients with null mutations of OTC. In summary, the OTC knockout (KO) model generated in our laboratory through the deletion of exons 2-3 closely mimics the severe neonatal onset form of OTCD in humans. Neonatal male OTC KO pups have elevated plasma ammonia levels due to the absence of OTC expression in the liver, and they inevitably die within 24 hours after birth. Heterozygous females breed normally, have normal plasma ammonia levels, reduced liver OTC enzyme activity, elevated urine orotic acid levels, and in some cases lower body weight compared to wild type (WT) littermates. A single injection of scAAV8-hOTCco vector prepared as described in Example 1 at a dose of 1-3×10e10 GC/pup immediately after birth is able to rescue the OTC KO pups and extend the life to 6 weeks. To achieve long-term correction, a group of 4-week-old OTC-KO mice received a second vector administration of scAAVrh10-hOTCco vector, which had been prepared as described in Example 1.

Over 30 OTC-KO pups retrieved by Cesarean section have been successfully rescued with gene delivery. The rescued pups had lower body weight than their normal littermates and had a transient phenotype of sparse fur and abnormal skin. Most importantly, their plasma ammonia levels were in the normal range. However, the efficacy cannot be maintained beyond 6 weeks due to loss of vector genome during fast liver proliferation in neonatal stage. A second vector administration of scAAVrh10-hOTCco vector in 4-week-old OTC-KO mice is able to further extend their lives to adulthood. The oldest mice have reached 18 months of age. The long-term rescued mice show close to normal levels of plasma ammonia, although urine orotic acid levels in a subset of these mice were significantly elevated. Sirius red staining on liver samples from heterozygous mice of different ages (6, 12, and 18 months old) showed liver fibrosis in aged (18-month old) OTC-KO heterozygous female mice, similar to a liver sample from a 11-year-old OTCD patient.

Example 10—Treatment of Late Onset OTC Deficiency (OTCD)

Two-month old OTC-KO heterozygous mice received a single tail vein injection of a self-complementary AAV8 vector encoding a codon-optimized human OTC gene (SEQ ID NO: 5) at $1\times10^{10}$, $3\times10^{10}$, and $1\times10^{11}$ vector genome copies per mouse. One week following vector treatment, mice in all three vector dose groups had normal urine orotic acid levels which were maintained throughout the study (16 months). Liver samples were harvested from 18 month old treated mice for pathology analysis and compared to age-matched untreated heterozygous mice and WT littermates. All treated mice showed normal liver histology similar to WT, in contrast to the untreated heterozygous animals which had fibrosis throughout the liver. In conclusion, a single injection of AAV8sc-hOTCco vector can prevent liver fibrosis in OTC-KO heterozygous and has great potential for correction of liver fibrosis in OTCD patients.

Gene therapy vectors described herein are capable of rapid, robust and prolonged gene expression even in mice with a complete lack of OTC. Heterozygous females are able to reproduce and deliver hemizygous male offspring, but these pups die within a day of birth if untreated. Untreated old heterozygous female mice show evidence of increased fibrosis and microvesicular steatosis, a finding that appears similar to observations in human heterozygous patients. A regimen of gene transfer that is able to rescue affected males has been developed and treated males have survived over 72 weeks.

Thus, these data demonstrate that liver-specific gene therapy with hOTC can prevent liver fibrosis. These data correlate with in treatment of heterozygous OTC deficient humans, e.g., subjects having late onset of OTCD.

Sequence Listing Free Text

The following information is provided for sequences containing free text under numeric identifier <223>.

| SEQ ID NO: (containing free text) | Free text under <223> |
|---|---|
| 3 | Engineered hOTC |
| 4 | Engineered hOTC |
| 5 | Engineered hOTC |
| 6 | Plasmid pscAAVTBGhOTCLW |
| 8 | Engineered hOTC |
| 9 | Engineered hOTC |
| 10 | Engineered hOTC RNA |
| 11 | Engineered hOTC RNA |
| 12 | Engineered hOTC RNA |
| 13 | Engineered hOTC RNA |
| 14 | PCR forward primer |
| 15 | PCR reverse primer |
| 16 | Probe |

The priority U.S. Provisional Patent Application No. 61/950,157, filed Mar. 9, 2014, and all published documents cited in this specification are incorporated herein by reference. Similarly, the SEQ ID NO which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

What is claimed is:

1. A composition comprising a non-viral carrier and a nucleic acid molecule comprising an engineered sequence encoding human ornithine transcarbamylase (hOTCase) and expression control sequences which direct expression of hOTCase in a liver cell, wherein the hOTC nucleic acid sequence is less than 80% identical to the wild-type hOTC sequence over at least the mature hOTC sequence of SEQ ID NO: 1, wherein said hOTC nucleic acid sequence is selected from the nucleic acid sequence comprising SEQ ID NO: 5 or a nucleic acid sequence at least about 96% identical thereto, a nucleic acid sequence selected from SEQ ID NO: 9, or a nucleic acid sequence at least about 96% identical thereto, a nucleic acid sequence comprising SEQ ID NO: 11 or a nucleic acid sequence at least about 96% identical thereto, or a nucleic acid sequence comprising SEQ ID NO: 13 or a nucleic acid sequence at least about 96% identical thereto.

2. The composition according to claim 1, wherein the hOTC nucleic acid sequence is a DNA sequence of SEQ ID NO: 4.

3. The composition according to claim 1, wherein the hOTC nucleic acid sequence is a DNA sequence of SEQ ID NO: 3.

4. The composition according to claim 1, wherein the hOTC nucleic acid sequence is a DNA sequence of SEQ ID NO: 8.

5. The composition according to claim 1, wherein the hOTC is an RNA sequence of SEQ ID NO: 10.

6. The composition according to claim 1, wherein the hOTC is an RNA sequence of SEQ ID NO: 12.

7. The composition according to claim 1, wherein the hOTC is a chimeric OTC which comprises a heterologous transit sequence substituted for the native transit sequence of SEQ ID NO: 5, 6, 7, 8, 9, 10, 11, 12 or 13.

8. The composition according to claim 1, wherein the expression control sequences further comprise a liver-specific promoter.

9. The composition according to claim 8, wherein the liver-specific promoter is selected from a thyroxin-binding globulin (TBG) promoter or a lymphocyte-specific protein 1 (LSP1) promoter.

10. The composition according to claim 1, wherein the expression cassette further comprises one or more of an intron, a Kozak sequence, a poly A, and a post-transcriptional regulatory elements.

11. The composition according to claim 1, wherein non-viral carrier is a plasmid.

12. The composition according to claim 11, wherein the plasmid has the sequence of SEQ ID NO: 6.

13. The composition according to claim 1, wherein the nucleic acid molecule is formulated in a moiety selected from the group consisting of micelles, liposomes, cationic lipid-nucleic acid compositions, poly-glycan compositions, block copolymers and other polymers, lipid and/or cholesterol-based-nucleic acid conjugates.

14. The composition according to claim 12, wherein the moiety is a nanoparticle.

15. A method for delivering ornithine transcarbamylase to a subject in need thereof and/or for treating ornithine transcarbamylase deficiency in a subject comprising delivering a composition according to claim 1 to a subject in need thereof.

* * * * *

UNITED STATES PATENT AND TRADEMARK OFFICE
CERTIFICATE OF CORRECTION

PATENT NO. : 9,890,365 B2
APPLICATION NO. : 15/124620
DATED : February 13, 2018
INVENTOR(S) : Lili Wang and James M. Wilson Page 1 of 1

It is certified that error appears in the above-identified patent and that said Letters Patent is hereby corrected as shown below:

Column 1, Lines 16-19, the paragraph under the heading "STATEMENT REGARDING FEDERALLY SPONSORED RESEARCH OR DEVELOPMENT" is replaced by the following paragraph:
-- This invention was made with government support under grant numbers HD057247, HL059407 and DK047757 awarded by the National Institutes of Health. The government has certain rights in the invention. --

Signed and Sealed this
Eighteenth Day of June, 2019

Andrei Iancu
*Director of the United States Patent and Trademark Office*

SEQUENCE LISTING

<160> NUMBER OF SEQ ID NOS: 16

<210> SEQ ID NO 1
<211> LENGTH: 1062
<212> TYPE: DNA
<213> ORGANISM: homo sapiens
<220> FEATURE:
<221> NAME/KEY: CDS
<222> LOCATION: (1)..(1062)

<400> SEQUENCE: 1

| | | | | | | | | | | | | | | | | |
|---|---|---|---|---|---|---|---|---|---|---|---|---|---|---|---|---|
| atg | ctg | ttt | aat | ctg | agg | atc | ctg | tta | aac | aat | gca | gct | ttt | aga | aat | 48 |
| Met | Leu | Phe | Asn | Leu | Arg | Ile | Leu | Leu | Asn | Asn | Ala | Ala | Phe | Arg | Asn | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggt | cac | aac | ttc | atg | gtt | cga | aat | ttt | cgg | tgt | gga | caa | cca | cta | caa | 96 |
| Gly | His | Asn | Phe | Met | Val | Arg | Asn | Phe | Arg | Cys | Gly | Gln | Pro | Leu | Gln | |
| | | | 20 | | | | | 25 | | | | | 30 | | | |

| | | | | | | | | | | | | | | | | |
|---|---|---|---|---|---|---|---|---|---|---|---|---|---|---|---|---|
| aat | aaa | gtg | cag | ctg | aag | ggc | cgt | gac | ctt | ctc | act | cta | aaa | aac | ttt | 144 |
| Asn | Lys | Val | Gln | Leu | Lys | Gly | Arg | Asp | Leu | Leu | Thr | Leu | Lys | Asn | Phe | |
| | | 35 | | | | | 40 | | | | | 45 | | | | |

| | | | | | | | | | | | | | | | | |
|---|---|---|---|---|---|---|---|---|---|---|---|---|---|---|---|---|
| acc | gga | gaa | gaa | att | aaa | tat | atg | cta | tgg | cta | tca | gca | gat | ctg | aaa | 192 |
| Thr | Gly | Glu | Glu | Ile | Lys | Tyr | Met | Leu | Trp | Leu | Ser | Ala | Asp | Leu | Lys | |
| | 50 | | | | | 55 | | | | | 60 | | | | | |

| | | | | | | | | | | | | | | | | |
|---|---|---|---|---|---|---|---|---|---|---|---|---|---|---|---|---|
| ttt | agg | ata | aaa | cag | aaa | gga | gag | tat | ttg | cct | tta | ttg | caa | ggg | aag | 240 |
| Phe | Arg | Ile | Lys | Gln | Lys | Gly | Glu | Tyr | Leu | Pro | Leu | Leu | Gln | Gly | Lys | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tcc | tta | ggc | atg | att | ttt | gag | aaa | aga | agt | act | cga | aca | aga | ttg | tct | 288 |
| Ser | Leu | Gly | Met | Ile | Phe | Glu | Lys | Arg | Ser | Thr | Arg | Thr | Arg | Leu | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| aca | gaa | aca | ggc | ttt | gca | ctt | ctg | gga | gga | cat | cct | tgt | ttt | ctt | acc | 336 |
| Thr | Glu | Thr | Gly | Phe | Ala | Leu | Leu | Gly | Gly | His | Pro | Cys | Phe | Leu | Thr | |
| | | | 100 | | | | | 105 | | | | | 110 | | | |

| | | | | | | | | | | | | | | | | |
|---|---|---|---|---|---|---|---|---|---|---|---|---|---|---|---|---|
| aca | caa | gat | att | cat | ttg | ggt | gtg | aat | gaa | agt | ctc | acg | gac | acg | gcc | 384 |
| Thr | Gln | Asp | Ile | His | Leu | Gly | Val | Asn | Glu | Ser | Leu | Thr | Asp | Thr | Ala | |
| | | 115 | | | | | 120 | | | | | 125 | | | | |

| | | | | | | | | | | | | | | | | |
|---|---|---|---|---|---|---|---|---|---|---|---|---|---|---|---|---|
| cgt | gta | ttg | tct | agc | atg | gca | gat | gca | gta | ttg | gct | cga | gtg | tat | aaa | 432 |
| Arg | Val | Leu | Ser | Ser | Met | Ala | Asp | Ala | Val | Leu | Ala | Arg | Val | Tyr | Lys | |
| | 130 | | | | | 135 | | | | | 140 | | | | | |

| | | | | | | | | | | | | | | | | |
|---|---|---|---|---|---|---|---|---|---|---|---|---|---|---|---|---|
| caa | tca | gat | ttg | gac | acc | ctg | gct | aaa | gaa | gca | tcc | atc | cca | att | atc | 480 |
| Gln | Ser | Asp | Leu | Asp | Thr | Leu | Ala | Lys | Glu | Ala | Ser | Ile | Pro | Ile | Ile | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| aat | ggg | ctg | tca | gat | ttg | tac | cat | cct | atc | cag | atc | ctg | gct | gat | tac | 528 |
| Asn | Gly | Leu | Ser | Asp | Leu | Tyr | His | Pro | Ile | Gln | Ile | Leu | Ala | Asp | Tyr | |
| | | | | 165 | | | | | 170 | | | | | 175 | | |

| | | | | | | | | | | | | | | | | |
|---|---|---|---|---|---|---|---|---|---|---|---|---|---|---|---|---|
| ctc | acg | ctc | cag | gaa | cac | tat | agc | tct | ctg | aaa | ggt | ctt | acc | ctc | agc | 576 |
| Leu | Thr | Leu | Gln | Glu | His | Tyr | Ser | Ser | Leu | Lys | Gly | Leu | Thr | Leu | Ser | |
| | | | 180 | | | | | 185 | | | | | 190 | | | |

| | | | | | | | | | | | | | | | | |
|---|---|---|---|---|---|---|---|---|---|---|---|---|---|---|---|---|
| tgg | atc | ggg | gat | ggg | aac | aat | atc | ctg | cac | tcc | atc | atg | atg | agc | gca | 624 |
| Trp | Ile | Gly | Asp | Gly | Asn | Asn | Ile | Leu | His | Ser | Ile | Met | Met | Ser | Ala | |
| | | 195 | | | | | 200 | | | | | 205 | | | | |

| | | | | | | | | | | | | | | | | |
|---|---|---|---|---|---|---|---|---|---|---|---|---|---|---|---|---|
| gcg | aaa | ttc | gga | atg | cac | ctt | cag | gca | gct | act | cca | aag | ggt | tat | gag | 672 |
| Ala | Lys | Phe | Gly | Met | His | Leu | Gln | Ala | Ala | Thr | Pro | Lys | Gly | Tyr | Glu | |
| | 210 | | | | | 215 | | | | | 220 | | | | | |

| | | | | | | | | | | | | | | | | |
|---|---|---|---|---|---|---|---|---|---|---|---|---|---|---|---|---|
| ccg | gat | gct | agt | gta | acc | aag | ttg | gca | gag | cag | tat | gcc | aaa | gag | aat | 720 |
| Pro | Asp | Ala | Ser | Val | Thr | Lys | Leu | Ala | Glu | Gln | Tyr | Ala | Lys | Glu | Asn | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ggt | acc | aag | ctg | ttg | ctg | aca | aat | gat | cca | ttg | gaa | gca | gcg | cat | gga | 768 |
| Gly | Thr | Lys | Leu | Leu | Leu | Thr | Asn | Asp | Pro | Leu | Glu | Ala | Ala | His | Gly | |
| | | | | 245 | | | | | 250 | | | | | 255 | | |

| | | | | | | | | | | | | | | | | |
|---|---|---|---|---|---|---|---|---|---|---|---|---|---|---|---|---|
| ggc | aat | gta | tta | att | aca | gac | act | tgg | ata | agc | atg | gga | caa | gaa | gag | 816 |
| Gly | Asn | Val | Leu | Ile | Thr | Asp | Thr | Trp | Ile | Ser | Met | Gly | Gln | Glu | Glu | |

|  |  |  |  |  |  |  |  |  |  |  |  |  |  |  |  |  |
|---|---|---|---|---|---|---|---|---|---|---|---|---|---|---|---|---|
|  |  |  |  | 260 |  |  |  |  | 265 |  |  |  |  | 270 |  |  |
| gag | aag | aaa | aag | cgg | ctc | cag | gct | ttc | caa | ggt | tac | cag | gtt | aca | atg | 864 |
| Glu | Lys | Lys | Lys | Arg | Leu | Gln | Ala | Phe | Gln | Gly | Tyr | Gln | Val | Thr | Met |  |
|  |  |  | 275 |  |  |  |  | 280 |  |  |  |  | 285 |  |  |  |
| aag | act | gct | aaa | gtt | gct | gcc | tct | gac | tgg | aca | ttt | tta | cac | tgc | ttg | 912 |
| Lys | Thr | Ala | Lys | Val | Ala | Ala | Ser | Asp | Trp | Thr | Phe | Leu | His | Cys | Leu |  |
|  | 290 |  |  |  |  | 295 |  |  |  |  | 300 |  |  |  |  |  |
| ccc | aga | aag | cca | gaa | gaa | gtg | gat | gat | gaa | gtc | ttt | tat | tct | cct | cga | 960 |
| Pro | Arg | Lys | Pro | Glu | Glu | Val | Asp | Asp | Glu | Val | Phe | Tyr | Ser | Pro | Arg |  |
| 305 |  |  |  |  | 310 |  |  |  |  | 315 |  |  |  |  | 320 |  |
| tca | cta | gtg | ttc | cca | gag | gca | gaa | aac | aga | aag | tgg | aca | atc | atg | gct | 1008 |
| Ser | Leu | Val | Phe | Pro | Glu | Ala | Glu | Asn | Arg | Lys | Trp | Thr | Ile | Met | Ala |  |
|  |  |  |  | 325 |  |  |  |  | 330 |  |  |  |  | 335 |  |  |
| gtc | atg | gtg | tcc | ctg | ctg | aca | gat | tac | tca | cct | cag | ctc | cag | aag | cct | 1056 |
| Val | Met | Val | Ser | Leu | Leu | Thr | Asp | Tyr | Ser | Pro | Gln | Leu | Gln | Lys | Pro |  |
|  |  |  | 340 |  |  |  |  | 345 |  |  |  |  | 350 |  |  |  |
| aaa | ttt |  |  |  |  |  |  |  |  |  |  |  |  |  |  | 1062 |
| Lys | Phe |  |  |  |  |  |  |  |  |  |  |  |  |  |  |  |

<210> SEQ ID NO 2
<211> LENGTH: 354
<212> TYPE: PRT
<213> ORGANISM: homo sapiens

<400> SEQUENCE: 2

Met Leu Phe Asn Leu Arg Ile Leu Leu Asn Asn Ala Ala Phe Arg Asn
1               5                   10                  15

Gly His Asn Phe Met Val Arg Asn Phe Arg Cys Gly Gln Pro Leu Gln
            20                  25                  30

Asn Lys Val Gln Leu Lys Gly Arg Asp Leu Leu Thr Leu Lys Asn Phe
        35                  40                  45

Thr Gly Glu Glu Ile Lys Tyr Met Leu Trp Leu Ser Ala Asp Leu Lys
    50                  55                  60

Phe Arg Ile Lys Gln Lys Gly Glu Tyr Leu Pro Leu Leu Gln Gly Lys
65                  70                  75                  80

Ser Leu Gly Met Ile Phe Glu Lys Arg Ser Thr Arg Thr Arg Leu Ser
                85                  90                  95

Thr Glu Thr Gly Phe Ala Leu Leu Gly Gly His Pro Cys Phe Leu Thr
            100                 105                 110

Thr Gln Asp Ile His Leu Gly Val Asn Glu Ser Leu Thr Asp Thr Ala
        115                 120                 125

Arg Val Leu Ser Ser Met Ala Asp Ala Val Leu Ala Arg Val Tyr Lys
    130                 135                 140

Gln Ser Asp Leu Asp Thr Leu Ala Lys Glu Ala Ser Ile Pro Ile Ile
145                 150                 155                 160

Asn Gly Leu Ser Asp Leu Tyr His Pro Ile Gln Ile Leu Ala Asp Tyr
                165                 170                 175

Leu Thr Leu Gln Glu His Tyr Ser Ser Leu Lys Gly Leu Thr Leu Ser
            180                 185                 190

Trp Ile Gly Asp Gly Asn Asn Ile Leu His Ser Ile Met Met Ser Ala
        195                 200                 205

Ala Lys Phe Gly Met His Leu Gln Ala Ala Thr Pro Lys Gly Tyr Glu
    210                 215                 220

Pro Asp Ala Ser Val Thr Lys Leu Ala Glu Gln Tyr Ala Lys Glu Asn
225                 230                 235                 240

Gly Thr Lys Leu Leu Leu Thr Asn Asp Pro Leu Glu Ala Ala His Gly

```
                   245                 250                 255
Gly Asn Val Leu Ile Thr Asp Thr Trp Ile Ser Met Gly Gln Glu Glu
            260                 265                 270

Glu Lys Lys Lys Arg Leu Gln Ala Phe Gln Gly Tyr Gln Val Thr Met
        275                 280                 285

Lys Thr Ala Lys Val Ala Ala Ser Asp Trp Thr Phe Leu His Cys Leu
    290                 295                 300

Pro Arg Lys Pro Glu Glu Val Asp Asp Glu Val Phe Tyr Ser Pro Arg
305                 310                 315                 320

Ser Leu Val Phe Pro Glu Ala Glu Asn Arg Lys Trp Thr Ile Met Ala
                325                 330                 335

Val Met Val Ser Leu Leu Thr Asp Tyr Ser Pro Gln Leu Gln Lys Pro
            340                 345                 350

Lys Phe

<210> SEQ ID NO 3
<211> LENGTH: 1068
<212> TYPE: DNA
<213> ORGANISM: Artificial sequence
<220> FEATURE:
<223> OTHER INFORMATION: engineered hOTC

<400> SEQUENCE: 3
atgctgttca acctgcgaat cctgctgaac aatgccgctt ttcggaacgg gcacaatttc        60
atggtgagga actttcgctg cggacagccc ctccagaaca aggtccagct gaagggcagg       120
gacctgctga ccctgaaaaa tttcacaggg gaggaaatca agtacatgct gtggctgtca       180
gccgatctga agttccggat caagcagaag ggcgaatatc tgcctctgct ccagggcaaa       240
agcctgggga tgatcttcga aaagcgcagt actcggacca gactgtcaac agagactgga       300
ttcgcactgc tgggaggaca cccatgtttt ctgaccacac aggacattca tctgggagtg       360
aacgagtccc tgaccgacac agcacgcgtc ctgagctcca tggctgatgc agtgctggct       420
cgagtctaca acagtctgac ctggataccc tggccaagg aagcttctat cccaatcatt        480
aatggcctga gtgacctgta tcaccccatc cagattctgg ccgattacct gacccctcca       540
gagcattatt ctagtctgaa agggctgaca ctgagctgga ttggggacgg aaacaatatc       600
ctgcactcca ttatgatgag cgccgccaag tttggaatgc acctccaggc tgcaacccca       660
aaaggctacg aacccgatgc ctccgtgaca aagctggcag aacagtatgc caaagagaac       720
ggcactaagc tgctgctgac caatgaccct ctggaggccg ctcacggagg caacgtgctg       780
atcactgata cctggattag tatgggacag gaggaagaga agaagaagcg gctccaggcc       840
ttccagggct accaggtgac aatgaaaact gctaaggtcg cagccagcga ctggaccttt       900
ctgcattgcc tgcccagaaa gcctgaagag gtggacgatg aggtcttcta ctcacccaga       960
agcctggtgt tcctgaagc tgagaatagg aagtggacaa tcatggcagt gatggtcagc      1020
ctgctgactg attattcccc tcagctccag aaaccaaagt tctgataa                 1068

<210> SEQ ID NO 4
<211> LENGTH: 1068
<212> TYPE: DNA
<213> ORGANISM: Artificial sequence
<220> FEATURE:
<223> OTHER INFORMATION: engineered hOTC coding sequence

<400> SEQUENCE: 4 atgctgtttca acctgcgaat cctgctgaac aacgccgctt ttcggaacgg gcacaacttt        60
```

```
atggtgagga actttcgctg cggacagccc ctccagaata aggtccagct gaagggcagg      120
gacctgctga ccctgaaaaa tttcacaggg gaggaaatca gtatatgct gtggctgtca       180 gctgatctga agttccggat caagcagaag ggcgaatatc tgcctctgct ccagggcaaa      240
agcctgggga tgatcttcga aaagcgcagt actcggacca gactgtcaac cgagactgga     300
ttcgctctgc tgggaggaca cccttgtttt ctgaccactc aggacattca cctgggagtg     360
aacgagtccc tgaccgacac tgctcgcgtc ctgagctcta tggccgacgc tgtgctagct     420
cgagtctaca acagtccga cctggatacc ctggccaagg aagcttctat cccaattatt      480 aacgcctgt cagacctgta tcaccccatc cagattctgg ccgattacct gaccctccag       540
gagcactatt ctagtctgaa agggctgaca ctgagttgga ttggggacgg aaacaatatc     600
ctgcactcta ttatgatgtc agccgccaag tttggaatgc acctccaggc tgcaaccca      660 aaaggctacg aacccgatgc ctcagtgaca aagctggctg aacagtacgc caaagagaac     720
ggcactaagc tgctgctgac caacgaccct ctggaggccg ctcacggagg caacgtgctg     780
atcaccgata cctggattag tatgggacag gaggaagaga agaagaagcg gctccaggcc     840
ttccagggct accaggtgac aatgaaaacc gctaaggtcg cagccagcga ttggaccttt    900
ctgcactgcc tgcccagaaa gcccgaagag gtggacgacg aggtcttcta ctctcccaga    960
agcctggtgt tccccgaagc tgagaatagg aagtggacaa ttatggcagt gatggtcagc   1020
ctgctgactg attattcacc tcagctccag aaaccaaagt tctgataa               1068
```

<210> SEQ ID NO 5
<211> LENGTH: 1068
<212> TYPE: DNA
<213> ORGANISM: Artificial sequence
<220> FEATURE:
<223> OTHER INFORMATION: engineered hOTC

<400> SEQUENCE: 5

```
atgctgttca acctgcgaat cctgctgaac aacgccgctt tcggaacgg gcacaacttt       60 atggtgagga actttcgctg cggacagccc ctccagaata aggtccagct gaagggcagg    120
gacctgctga ccctgaaaaa tttcacaggg gaggaaatca gtatatgct gtggctgtca     180 gctgatctga agttccggat caagcagaag ggcgaatatc tgcctctgct ccagggcaaa    240
agcctgggga tgatcttcga aaagcgcagt actcggacca gactgtcaac cgagactgga   300
ttcgctctgc tgggaggaca cccttgtttt ctgaccactc aggacattca cctgggagtg   360
aacgagtccc tgaccgacac tgctcgcgtc ctgagctcta tggccgacgc tgtgctggct   420
cgagtctaca acagtccga cctggatacc ctggccaagg aagcttctat cccaattatt    480 aacgcctgt cagacctgta tcaccccatc cagattctgg ccgattacct gaccctccag     540
gagcactatt ctagtctgaa agggctgaca ctgagttgga ttggggacgg aaacaatatc   600
ctgcactcta ttatgatgtc agccgccaag tttggaatgc acctccaggc tgcaaccca    660 aaaggctacg aacccgatgc ctcagtgaca aagctggctg aacagtacgc caaagagaac   720
ggcactaagc tgctgctgac caacgaccct ctggaggccg ctcacggagg caacgtgctg   780
atcaccgata cctggattag tatgggacag gaggaagaga agaagaagcg gctccaggcc   840
ttccagggct accaggtgac aatgaaaacc gctaaggtcg cagccagcga ttggaccttt   900
ctgcactgcc tgcccagaaa gcccgaagag gtggacgacg aggtcttcta ctctcccaga   960
agcctggtgt tccccgaagc tgagaatagg aagtggacaa ttatggcagt gatggtcagc  1020
```

-continued ctgctgactg attattcacc tcagctccag aaaccaaagt tctgataa                1068

<210> SEQ ID NO 6
<211> LENGTH: 5195
<212> TYPE: DNA
<213> ORGANISM: Artificial sequence
<220> FEATURE:
<223> OTHER INFORMATION: Plasmid pscAAVTBGhOTCLW
<220> FEATURE:
<221> NAME/KEY: repeat_region
<222> LOCATION: (5)..(109)
<223> OTHER INFORMATION: ITR
<220> FEATURE:
<221> NAME/KEY: TATA_signal
<222> LOCATION: (851)..(854)
<220> FEATURE:
<221> NAME/KEY: CDS
<222> LOCATION: (976)..(2037)
<223> OTHER INFORMATION: hOTCco-LW4
<220> FEATURE:
<221> NAME/KEY: polyA
<222> LOCATION: (2046)..(2182)
<223> OTHER INFORMATION: ITR, located on complement
<220> FEATURE:
<221> NAME/KEY: repeat_region
<222> LOCATION: (2211)..(2378)
<223> OTHER INFORMATION: ITR, located on complement
<220> FEATURE:
<221> NAME/KEY: misc_feature
<222> LOCATION: (4172)..(4760)
<223> OTHER INFORMATION: TBG/promoter

<400> SEQUENCE: 6
taggctgcgc gctcgctcgc tcactgaggc cgcccgggca aagcccgggc gtcgggcgac    60
ctttggtcgc ccggcctcag tgagcgagcg agcgcgcaga gagggagtgt agccatgctc   120
taggaagatc aattcaattc acgcgtggta cctagaacta tagctagaat tcgcccttaa   180
gctagcaggt taattttta aaaagcagtca aaagtccaag tggcccttgg cagcatttac   240
tctctctgtt tgctctggtt aataatctca ggagcacaaa cattccagat ccaggttaat   300
ttttaaaaag cagtcaaaag tccaagtggc ccttggcagc atttactctc tctgttttgct   360 ctggttaata atctcaggag cacaaacatt ccagatccgg cgcgccaggg ctggaagcta   420
cctttgacat catttcctct gcgaatgcat gtataatttc tacagaacct attagaaagg   480
atcacccagc ctctgctttt gtacaacttt cccttaaaaa actgccaatt ccactgctgt   540
ttggcccaat agtgagaact ttttcctgct gcctcttggt gcttttgcct atggccccta   600
ttctgcctgc tgaagacact cttgccagca tggacttaaa cccctccagc tctgacaatc   660
ctctttctct tttgttttac atgaagggtc tggcagccaa agcaatcact caaagttcaa   720
accttatcat tttttgcttt gttcctcttg gccttggttt tgtacatcag ctttgaaaat   780
accatcccag ggttaatgct ggggttaatt tataactaag agtgctctag ttttgcaata   840
caggacatgc tataaaaatg gaaagatgtt gctttctgag agacagcttt attgcggtag   900
tttatcacag ttaaattgct aacgcagtca gtgcttctga cacaacagtc tcgaacttaa   960
gctgcagccg ccacc atg ctg ttc aac ctg cga atc ctg ctg aac aac gcc   1011
              Met Leu Phe Asn Leu Arg Ile Leu Leu Asn Asn Ala
                1               5                  10 gct ttt cgg aac ggg cac aac ttt atg gtg agg aac ttt cgc tgc gga    1059
Ala Phe Arg Asn Gly His Asn Phe Met Val Arg Asn Phe Arg Cys Gly
        15                  20                  25 cag ccc ctc cag aat aag gtc cag ctg aag ggc agg gac ctg ctg acc    1107
Gln Pro Leu Gln Asn Lys Val Gln Leu Lys Gly Arg Asp Leu Leu Thr
    30                  35                  40

```
ctg aaa aat ttc aca ggg gag gaa atc aag tat atg ctg tgg ctg tca    1155
Leu Lys Asn Phe Thr Gly Glu Glu Ile Lys Tyr Met Leu Trp Leu Ser
 45                  50                  55                  60 gct gat ctg aag ttc cgg atc aag cag aag ggc gaa tat ctg cct ctg    1203
Ala Asp Leu Lys Phe Arg Ile Lys Gln Lys Gly Glu Tyr Leu Pro Leu
                 65                  70                  75 ctc cag ggc aaa agc ctg ggg atg atc ttc gaa aag cgc agt act cgg    1251
Leu Gln Gly Lys Ser Leu Gly Met Ile Phe Glu Lys Arg Ser Thr Arg
             80                  85                  90 acc aga ctg tca acc gag act gga ttc gct ctg cta gga gga cac cct    1299
Thr Arg Leu Ser Thr Glu Thr Gly Phe Ala Leu Leu Gly Gly His Pro
         95                 100                 105 tgt ttt ctg acc act cag gac att cac ctg gga gtg aac gag tcc ctg    1347
Cys Phe Leu Thr Thr Gln Asp Ile His Leu Gly Val Asn Glu Ser Leu
    110                 115                 120 acc gac act gct cgc gtc ctg agc tct atg gcc gac gct gtg ctg gct    1395
Thr Asp Thr Ala Arg Val Leu Ser Ser Met Ala Asp Ala Val Leu Ala
125                 130                 135                 140 cga gtc tac aaa cag tcc gac ctg gat acc ctg gcc aag gaa gct tct    1443
Arg Val Tyr Lys Gln Ser Asp Leu Asp Thr Leu Ala Lys Glu Ala Ser
                145                 150                 155 atc cca att att aac ggc ctg tca gac ctg tat cac ccc atc cag att    1491
Ile Pro Ile Ile Asn Gly Leu Ser Asp Leu Tyr His Pro Ile Gln Ile
            160                 165                 170 ctg gcc gat tac ctg acc ctc cag gag cac tat tct agt ctg aaa ggg    1539
Leu Ala Asp Tyr Leu Thr Leu Gln Glu His Tyr Ser Ser Leu Lys Gly
        175                 180                 185 ctg aca ctg agt tgg att ggg gac gga aac aat atc ctg cac tct att    1587
Leu Thr Leu Ser Trp Ile Gly Asp Gly Asn Asn Ile Leu His Ser Ile
    190                 195                 200 atg atg tca gcc gcc aag ttt gga atg cac ctc cag gct gca acc cca    1635
Met Met Ser Ala Ala Lys Phe Gly Met His Leu Gln Ala Ala Thr Pro
205                 210                 215                 220 aaa ggc tac gaa ccc gat gcc tca gtg aca aag ctg gct gaa cag tac    1683
Lys Gly Tyr Glu Pro Asp Ala Ser Val Thr Lys Leu Ala Glu Gln Tyr
                225                 230                 235 gcc aaa gag aac ggc act aag ctg ctg ctg acc aac gac cct ctg gag    1731
Ala Lys Glu Asn Gly Thr Lys Leu Leu Leu Thr Asn Asp Pro Leu Glu
            240                 245                 250 gcc gct cac gga ggc aac gtg ctg atc acc gat acc tgg att agt atg    1779
Ala Ala His Gly Gly Asn Val Leu Ile Thr Asp Thr Trp Ile Ser Met
        255                 260                 265 gga cag gag gaa gag aag aag aag cgg ctc cag gcc ttc cag ggc tac    1827
Gly Gln Glu Glu Glu Lys Lys Lys Arg Leu Gln Ala Phe Gln Gly Tyr
    270                 275                 280 cag gtg aca atg aaa acc gct aag gtc gca gcc agc gat tgg acc ttt    1875
Gln Val Thr Met Lys Thr Ala Lys Val Ala Ala Ser Asp Trp Thr Phe
285                 290                 295                 300 ctg cac tgc ctg ccc aga aag ccc gaa gag gtg gac gac gag gtc ttc    1923
Leu His Cys Leu Pro Arg Lys Pro Glu Glu Val Asp Asp Glu Val Phe
                305                 310                 315 tac tct ccc aga agc ctg gtg ttt ccc gaa gct gag aat agg aag tgg    1971
Tyr Ser Pro Arg Ser Leu Val Phe Pro Glu Ala Glu Asn Arg Lys Trp
            320                 325                 330 aca att atg gca gtg atg gtc agc ctg ctg act gat tat tca cct cag    2019
Thr Ile Met Ala Val Met Val Ser Leu Leu Thr Asp Tyr Ser Pro Gln
        335                 340                 345 ctc cag aaa cca aag ttc tgataagcgg ccgctatttg tgaaatttgt           2067
Leu Gln Lys Pro Lys Phe
        350
```

```
gatgctattg ctttatttgt aaccattata agctgcaata aacaagttaa caacaacaat    2127
tgcattcatt ttatgtttca ggttcagggg gaggtgtggg aggttttta ggcatcgata     2187 aggatcttcc tagagcatgg ctacgtagat aagtagcatg gcgggttaat cattaactac    2247
aaggaacccc tagtgatgga gttggccact ccctctctgc gcgctcgctc gctcactgag    2307
gccgggcgac caaaggtcgc ccgacgcccg ggctttgccc gggcggcctc agtgagcgag    2367
cgagcgcgca gccttaatta acctaattca ctggccgtcg ttttacaacg tcgtgactgg    2427
gaaaaccctg gcgttaccca acttaatcgc cttgcagcac atcccccttt cgccagctgg    2487
cgtaatagcg aagaggcccg caccgatcgc ccttcccaac agttgcgcag cctgaatggc    2547
gaatgggacg cgccctgtag cggcgcatta agcgcggcgg gtgtggtggt tacgcgcagc    2607
gtgaccgcta cacttgccag cgccctagcg cccgctcctt tcgctttctt cccttccttt    2667
ctcgccacgt tcgccggctt tccccgtcaa gctctaaatc gggggctccc tttagggttc    2727
cgatttagtg ctttacggca cctcgacccc aaaaaacttg attagggtga tggttcacgt    2787
agtgggccat cgccctgata gacggttttt cgccctttga cgttggagtc cacgttcttt    2847
aatagtggac tcttgttcca aactggaaca acactcaacc ctatctcggt ctattctttt    2907
gatttataag ggattttgcc gatttcggcc tattggttaa aaaatgagct gatttaacaa    2967
aaatttaacg cgaattttaa caaaatatta acgcttacaa tttaggtggc acttttcggg    3027
gaaatgtgcg cggaacccct atttgtttat ttttctaaat acattcaaat atgtatccgc    3087
tcatgagaca ataaccctga taaatgcttc aataatattg aaaaaggaag agtatgagta    3147
ttcaacattt ccgtgtcgcc cttattccct tttttgcggc attttgcctt cctgtttttg    3207
ctcacccaga aacgctggtg aaagtaaaag atgctgaaga tcagttgggt gcacgagtgg    3267
gttacatcga actggatctc aacagcggta agatccttga gagttttcgc cccgaagaac    3327
gttttccaat gatgagcact tttaaagttc tgctatgtgg cgcggtatta cccgtattg    3387 acgccgggca agagcaactc ggtcgccgca tacactattc tcagaatgac ttggttgagt    3447
actcaccagt cacagaaaag catcttacgg atggcatgac agtaagagaa ttatgcagtg    3507
ctgccataac catgagtgat aacactgcgg ccaacttact tctgacaacg atcggaggac    3567
cgaaggagct aaccgctttt ttgcacaaca tgggggatca tgtaactcgc cttgatcgtt    3627
gggaaccgga gctgaatgaa gccataccaa acgacgagcg tgacaccacg atgcctgtag    3687
caatggcaac aacgttgcgc aaactattaa ctggcgaact acttactcta gcttcccggc    3747
aacaattaat agactggatg gaggcggata agttgcagg accacttctg cgctcggccc     3807
ttccggctgg ctggtttatt gctgataaat ctggagccgg tgagcgtggg tctcgcggta    3867
tcattgcagc actggggcca gatggtaagc cctcccgtat cgtagttatc tacacgacgg    3927
ggagtcaggc aactatggat gaacgaaata cagatcgc tgagataggt gcctcactga      3987
ttaagcattg gtaactgtca gaccaagttt actcatatat actttagatt gatttaaaac    4047 ttcatttta atttaaaagg atctaggtga agatcctttt tgataatctc atgaccaaaa     4107
tcccttaacg tgagttttcg ttccactgag cgtcagaccc cgtagaaaag atcaaaggat    4167
cttcttgaga tccttttttt ctgcgcgtaa tctgctgctt gcaaacaaaa aaaccaccgc    4227
taccagcggt ggtttgtttg ccggatcaag agctaccaac tctttttccg aaggtaactg    4287
gcttcagcag agcgcagata ccaaatactg ttcttctagt gtagccgtag ttaggccacc    4347
acttcaagaa ctctgtagca ccgcctacat acctcgctct gctaatcctg ttaccagtgg    4407
```

```
ctgctgccag tggcgataag tcgtgtctta ccgggttgga ctcaagacga tagttaccgg    4467
ataaggcgca gcggtcgggc tgaacggggg gttcgtgcac acagcccagc ttggagcgaa    4527
cgacctacac cgaactgaga tacctacagc gtgagctatg agaaagcgcc acgcttcccg    4587
aagggagaaa ggcggacagg tatccggtaa gcggcagggt cggaacagga gagcgcacga    4647
gggagcttcc aggggaaac gcctggtatc tttatagtcc tgtcgggttt cgccacctct    4707
gacttgagcg tcgattttg tgatgctcgt caggggggcg gagcctatgg aaaaacgcca    4767
gcaacgcggc ctttttacgg ttcctggcct tttgctggcc ttttgctcac atgttctttc    4827
ctgcgttatc ccctgattct gtggataacc gtattaccgc ctttgagtga gctgataccg    4887
ctcgccgcag ccgaacgacc gagcgcagcg agtcagtgag cgaggaagcg gaagagcgcc    4947
caatacgcaa accgcctctc cccgcgcgtt ggccgattca ttaatgcagc tggcacgaca    5007
ggtttcccga ctggaaagcg ggcagtgagc gcaacgcaat taatgtgagt tagctcactc    5067
attaggcacc ccaggcttta cactttatgc ttccggctcg tatgttgtgt ggaattgtga    5127
gcggataaca atttcacaca ggaaacagct atgaccatga ttacgccaga tttaattaag    5187
gccttaat                                                           5195
```

<210> SEQ ID NO 7  
<211> LENGTH: 354  
<212> TYPE: PRT  
<213> ORGANISM: Artificial sequence  
<220> FEATURE:  
<223> OTHER INFORMATION: engineered hOTC
<400> SEQUENCE: 7

```
Met Leu Phe Asn Leu Arg Ile Leu Leu Asn Asn Ala Ala Phe Arg Asn
1               5                   10                  15

Gly His Asn Phe Met Val Arg Asn Phe Arg Cys Gly Gln Pro Leu Gln
            20                  25                  30

Asn Lys Val Gln Leu Lys Gly Arg Asp Leu Leu Thr Leu Lys Asn Phe
        35                  40                  45

Thr Gly Glu Glu Ile Lys Tyr Met Leu Trp Leu Ser Ala Asp Leu Lys
    50                  55                  60

Phe Arg Ile Lys Gln Lys Gly Glu Tyr Leu Pro Leu Leu Gln Gly Lys
65                  70                  75                  80

Ser Leu Gly Met Ile Phe Glu Lys Arg Ser Thr Arg Thr Arg Leu Ser
                85                  90                  95

Thr Glu Thr Gly Phe Ala Leu Leu Gly Gly His Pro Cys Phe Leu Thr
            100                 105                 110

Thr Gln Asp Ile His Leu Gly Val Asn Glu Ser Leu Thr Asp Thr Ala
        115                 120                 125

Arg Val Leu Ser Ser Met Ala Asp Ala Val Leu Ala Arg Val Tyr Lys
    130                 135                 140

Gln Ser Asp Leu Asp Thr Leu Ala Lys Glu Ala Ser Ile Pro Ile Ile
145                 150                 155                 160

Asn Gly Leu Ser Asp Leu Tyr His Pro Ile Gln Ile Leu Ala Asp Tyr
                165                 170                 175

Leu Thr Leu Gln Glu His Tyr Ser Ser Leu Lys Gly Leu Thr Leu Ser
            180                 185                 190

Trp Ile Gly Asp Gly Asn Asn Ile Leu His Ser Ile Met Met Ser Ala
        195                 200                 205

Ala Lys Phe Gly Met His Leu Gln Ala Ala Thr Pro Lys Gly Tyr Glu
    210                 215                 220
```

```
Pro Asp Ala Ser Val Thr Lys Leu Ala Glu Gln Tyr Ala Lys Glu Asn
225                 230                 235                 240

Gly Thr Lys Leu Leu Leu Thr Asn Asp Pro Leu Glu Ala Ala His Gly
                245                 250                 255

Gly Asn Val Leu Ile Thr Asp Thr Trp Ile Ser Met Gly Gln Glu Glu
            260                 265                 270

Glu Lys Lys Lys Arg Leu Gln Ala Phe Gln Gly Tyr Gln Val Thr Met
        275                 280                 285

Lys Thr Ala Lys Val Ala Ala Ser Asp Trp Thr Phe Leu His Cys Leu
    290                 295                 300

Pro Arg Lys Pro Glu Glu Val Asp Asp Glu Val Phe Tyr Ser Pro Arg
305                 310                 315                 320

Ser Leu Val Phe Pro Glu Ala Glu Asn Arg Lys Trp Thr Ile Met Ala
                325                 330                 335

Val Met Val Ser Leu Leu Thr Asp Tyr Ser Pro Gln Leu Gln Lys Pro
                340                 345                 350

Lys Phe

<210> SEQ ID NO 8
<211> LENGTH: 1065
<212> TYPE: DNA
<213> ORGANISM: Artificial sequence
<220> FEATURE:
<223> OTHER INFORMATION: engineered hOTC

<400> SEQUENCE: 8
atgctgttca acctgagaat cctgctgaac aacgccgcct tcagaaacgg ccacaacttc      60
atggtgagaa acttcagatg cggccagccc ctgcagaaca aggtgcagct gaagggcaga     120
gacctgctga ccctgaagaa cttcaccggc gaggagatca agtacatgct gtggctgagc     180
gccgacctga agttcagaat caagcagaag ggcgagtacc tgcccctgct gcagggcaag     240
agcctgggca tgatcttcga aagagaagc accagaacca gactgagcac cgagaccggc     300
ctggccctgc tggcggcca cccctgcttc ctgaccaccc aggacatcca cctgggcgtg     360
aacgagagcc tgaccgacac cgccagagtg ctgagcagca tggccgacgc cgtgctggcc     420
agagtgtaca gcagagcga cctggacacc ctggccaagg aggccagcat ccccatcatc     480 aacgcctga gcgacctgta ccaccccatc cagatcctgg ccgactacct gaccctgcag     540
gagcactaca gcagcctgaa gggcctgacc ctgagctgga tcggcgacgg caacaacatc     600
ctgcacagca tcatgatgag cgccgccaag ttcggcatgc acctgcaggc cgccaccccc     660
aagggctacg agcccgacgc cagcgtgacc aagctggccg agcagtacgc caaggagaac     720
ggcaccaagc tgctgctgac caacgacccc tggaggccg cccacggcgg caacgtgctg     780
atcaccgaca cctggatcag catgggccag gaggaggaga agaagaagag actgcaggcc     840
ttccagggct accaggtgac catgaagacc gccaaggtgg ccgccagcga ctggaccttc     900
ctgcactgcc tgcccagaaa gcccgaggag gtggacgacg aggtgttcta cagcccgaga    960
agcctggtgt tccccgaggc cgagaacaga aagtggacca tcatggccgt gatggtgagc    1020
ctgctgaccg actacagccc ccagctgcag aagcccaagt ctga                     1065

<210> SEQ ID NO 9
<211> LENGTH: 1065
<212> TYPE: DNA
<213> ORGANISM: Artificial sequence
<220> FEATURE:
```

<223> OTHER INFORMATION: engineered hOTC

<400> SEQUENCE: 9

```
atgctgttca acctgcgcat cctgctgaac aacgccgcct tccgcaacgg ccacaacttc       60
atggtgcgca acttccgctg cggccagccc ctgcagaaca aggtgcagct gaagggccgc      120
gacctgctga ccctgaagaa cttcaccggc gaggagatca agtacatgct gtggctgagc      180
gccgacctga agttccgcat caagcagaag ggcgagtacc tgcccctgct gcagggcaag      240
agcctgggca tgatcttcga aaagcgcagc acccgcaccc gcctgagcac cgagaccggc      300
ctggccctgc tgggcggcca ccctgcttc ctgaccaccc aggacatcca cctgggcgtg       360
aacgagagcc tgaccgacac cgcccgcgtg ctgagcagca tggccgacgc cgtgctggcc      420
cgcgtgtaca gcagagcga cctggacacc tggccaagg aggccagcat ccccatcatc        480
aacggcctga gcgacctgta ccaccccatc agatcctgg ccgactacct gaccctgcag       540
gagcactaca gcagcctgaa gggcctgacc ctgagctgga tcggcgacgg caacaacatc      600
ctgcacagca tcatgatgag cgccgccaag ttcggcatgc acctgcaggc cgccaccccc      660
aagggctacg agcccgacgc cagcgtgacc aagctggccg agcagtacgc caaggagaac      720
ggcaccaagc tgctgctgac caacgacccc ctggaggccg ccacggcgg caacgtgctg       780
atcaccgaca cctggatcag catgggccag gaggaggaga agaagaagcg cctgcaggcc      840
ttccagggct accaggtgac catgaagacc gccaaggtgg ccgccagcga ctggaccttc      900
ctgcactgcc tgccccgcaa gcccgaggag gtggacgacg aggtgttcta cagcccccgc      960
agcctggtgt tccccgaggc cgagaaccgc aagtggacca tcatggccgt gatggtgagc    1020
ctgctgaccg actacagccc ccagctgcag aagcccaagt tctga                    1065
```

<210> SEQ ID NO 10
<211> LENGTH: 1068
<212> TYPE: RNA
<213> ORGANISM: Artificial sequence
<220> FEATURE:
<223> OTHER INFORMATION: engineered hOTC RNA sequence

<400> SEQUENCE: 10

```
augcuguuca accugcgaau ccugcugaac aacgccgcuu uccggaacgg cacaacuuu       60
auggugagga acuuucgcug cggacagccc cuccagaaua agguccagcu gaagggcagg      120
gaccugcuga cccugaaaaa uuucacaggg gaggaaauca aguauaugcu gugcgcuca       180
gcugaucuga aguccggau caagcagaag ggcgaauauc ugccucugcu ccagggcaaa       240
agccugggga ugaucuucga aaagcgcagu acucggacca gacugucaac cgagacugga      300
uucgcucugc ugggaggaca cccuuguuuu cugaccacuc aggacauuca ccugggagug      360
aacgagucc ugaccgacac ugcucgcguc cugagcucua uggccgacgc ugugcuagcu       420
cgagucuaca acagucccga ccuggauacc cuggccaagg aagcuucuau cccaauuauu      480
aacggccugu cagaccugua ucaccccauc agauucugg ccgauuaccu gacccuccag       540
gagcacuauu cuaugucugaa agggcugaca cugaguugga uggggacgg aaacaauauc      600
cugcacucua uuaugaugu agccgccaag uuuggaaugc accucaggc ugcaacccca       660
aaaggcuacg aacccgaugc cucagugaca aagcuggcug aacaguacgc caaagagaac      720
ggcacuaagc ugcugcugac caacgacccu cuggaggccg cucacggagg caacgugcug      780
aucaccgaua ccuggauuag uauggacag gaggaagaga agaagaagcg gcuccaggcc       840
uuccagggcu accaggugac aaugaaaacc gcuaaggucg cagccagcga uuggaccuuu      900
```

```
cugcacugcc ugcccagaaa gcccgaagag guggacgacg aggucuucua cucucccaga    960
agccuggugu uucccgaagc ugagaauagg aaguggacaa uuauggcagu gauggucagc   1020
cugcugacug auuauucacc ucagcuccag aaaccaaagu ucugauaa                1068
```

<210> SEQ ID NO 11
<211> LENGTH: 1068
<212> TYPE: RNA
<213> ORGANISM: Artificial sequence
<220> FEATURE:
<223> OTHER INFORMATION: engineered hOTC RNA

<400> SEQUENCE: 11

```
augcuguuca accugcgaau ccugcugaac aacgccgcuu ucggaacgg gcacaacuuu     60 auggugagga acuuucgcug cggacagccc cuccagaaua aggucagcu gaagggcagg    120 gaccugcuga cccugaaaaa uuucacaggg gaggaaauca aguauaugcu guggcuguca    180
gcugaucuga aguccggau caagcagaag ggcgaauauc ugccucugcu ccagggcaaa    240 agccuggga ugaucuucga aaagcgcagu acucggacca gacugucaac cgagacugga    300
uucgcucugc ugggaggaca cccuuguuuu cugaccacuc aggacauuca ccugggagug    360
aacgagcccc ugaccgacac ugcucgcguc cugagcucua uggccgacgc ugugcuggcu    420
cgagucuaca aacaguccga ccuggauacc cuggccaagg aagcuucuau cccaauuauu    480
aacggccugu cagaccugua ucaccccauc cagauucugg ccgauuaccu gacccuccag    540
gagcacuauu cuagcugaa agggcugaca cugaguugga uuggggacgg aaacaauauc    600
cugcacucua uuaugauguc agccgccaag uuuggaaugc accuccaggc ugcaaccccca    660 aaaggcuacg aacccgaugc cucagugaca aagcuggcug aacaguacgc caaagagaac    720
ggcacuaagc ugcugcugac caacgacccu cuggaggccg ucacggagg caacgugcug    780 aucaccgaua ccuggauuag uaugggcacag gaggaagaga agaagaagcg gcuccaggcc    840
uuccagggcu accaggugac aaugaaaacc gcuaaggucg cagccagcga uuggaccuuu    900
cugcacugcc ugcccagaaa gcccgaagag guggacgacg aggucuucua cucucccaga    960
agccuggugu uucccgaagc ugagaauagg aaguggacaa uuauggcagu gauggucagc   1020
cugcugacug auuauucacc ucagcuccag aaaccaaagu ucugauaa                1068
```

<210> SEQ ID NO 12
<211> LENGTH: 1065
<212> TYPE: RNA
<213> ORGANISM: Artificial sequence
<220> FEATURE:
<223> OTHER INFORMATION: engineered hOTC

<400> SEQUENCE: 12

```
augcuguuca accugcgcau ccugcugaac aacgccgccu uccgcaacgg ccacaacuuc     60
auggugcgca acuuccgcug cggccagccc cugcagaaca aggugcagcu gaagggccgc    120
gaccugcuga cccugaagaa cuucaccggc gaggagauca aguacaugcu guggcugagc    180
gccgaccuga aguccgcau caagcagaag ggcgaguacc ugccccugcu cagggcaag    240 agccugggca ugaucuucga gaagcgcagc acccgcaccc gccugagcac cgagaccggc    300
cuggcccugc ugggcggcca cccugcuuc cugaccaccc aggacaucca ccugggcgug    360
aacgagagcc ugaccgacac cgcccgcgug cugagcagca uggccgacgc cgugcuggcc    420
cgcguguaca gcagagcga ccuggacacc cuggccaagg aggccagcau ccccaucauc    480
```

```
aacggccuga gcgaccugua ccaccccauc cagauccugg ccgacuaccu gaccgugcag    540
gagcacuaca gcagccugaa gggccugacc cugagcugga ucggcgacgg caacaacauc    600
cugcacagca ucaugaugag cgccgccaag uucggcaugc accugcaggc cgccaccccc    660
aagggcuacg agcccgacgc cagcgugacc aagcuggccg agcaguacgc caaggagaac    720
ggcaccaagc ugcugcugac caacgacccc cuggaggccc ccacggcgg caacgugcug    780 aucaccgaca ccuggaucag cauggccag gaggaggaga agaagaagcg ccugcaggcc    840
uuccagggcu accaggugac caugaagacc gccaaggugg ccgccagcga cuggaccuuc    900
cugcacugcc ugccccgcaa gcccgaggag guggacgacg agguguucua cagccccgc    960 agccuggugu uccccgaggc cgagaaccgc aaguggacca ucauggccgu gauggugagc   1020
cugcugaccg acuacagccc ccagcugcag aagcccaagu ucuga                  1065

<210> SEQ ID NO 13
<211> LENGTH: 1065
<212> TYPE: RNA
<213> ORGANISM: Artificial sequence
<220> FEATURE:
<223> OTHER INFORMATION: engineered hOTC

<400> SEQUENCE: 13
augcuguuca accugagaau ccugcugaac aacgccgccu ucagaaacgg ccacaacuuc     60
auggugagaa acuucagaug cggccagccc cugcagaaca aggugcagcu gaagggcaga   120
gaccugcuga cccugaagaa cuucaccggc gaggagauca aguacaugcu guggcugagc   180
gccgaccuga aguucagaau caagcagaag ggcgaguacc ugcccccugcu gcagggcaag   240 agccugggca ugaucuucga agagaagagc accagaacca gacugagcac cgagaccggc   300
cuggcccugc ugggcgggcca ccccugcuuc cugaccaccc aggacaucca ccugggcgug   360
aacgagagcc ugaccgacac cgccagagug cugagcagca uggccgacgc cgugcuggcc   420
agaguguaca agcagagcga ccuggacacc cuggccaagg aggccagcau ccccaucauc   480
aacggccuga gcgaccugua ccaccccauc cagauccugg ccgacuaccu gaccgugcag   540
gagcacuaca gcagccugaa gggccugacc cugagcugga ucggcgacgg caacaacauc   600
cugcacagca ucaugaugag cgccgccaag uucggcaugc accugcaggc cgccaccccc   660
aagggcuacg agcccgacgc cagcgugacc aagcuggccg agcaguacgc caaggagaac   720
ggcaccaagc ugcugcugac caacgacccc cuggaggccc ccacggcgg caacgugcug   780 aucaccgaca ccuggaucag cauggccag gaggaggaga agaagaagag acugcaggcc   840
uuccagggcu accaggugac caugaagacc gccaaggugg ccgccagcga cuggaccuuc   900
cugcacugcc ugcccagaaa gcccgaggag guggacgacg agguguucua cagccccaga   960
agccuggugu uccccgaggc cgagaacaga aaguggacca ucauggccgu gauggugagc  1020
cugcugaccg acuacagccc ccagcugcag aagcccaagu ucuga                 1065

<210> SEQ ID NO 14
<211> LENGTH: 21
<212> TYPE: DNA
<213> ORGANISM: Artificial sequence
<220> FEATURE:
<223> OTHER INFORMATION: PCR forward primer

<400> SEQUENCE: 14
aaactgccaa ttccactgct g                                            21
```

```
<210> SEQ ID NO 15
<211> LENGTH: 21
<212> TYPE: DNA
<213> ORGANISM: Artificial sequence
<220> FEATURE:
<223> OTHER INFORMATION: PCR reverse primer

<400> SEQUENCE: 15
ccataggcaa aagcaccaag a                                              21

<210> SEQ ID NO 16
<211> LENGTH: 29
<212> TYPE: DNA
<213> ORGANISM: Artificial Sequence
<220> FEATURE:
<223> OTHER INFORMATION: Probe

<400> SEQUENCE: 16
ttggcccaat agtgagaact ttttcctgc                                      29
```